United States Patent [19]
Leonard

[11] Patent Number: 6,113,782
[45] Date of Patent: Sep. 5, 2000

[54] POTTING OF TUBULAR BUNDLES IN HOUSING

[75] Inventor: Ronald J. Leonard, Ann Arbor, Mich.

[73] Assignee: Terumo Cardiovascular Systems Corporation, Somerset, N.J.

[21] Appl. No.: 09/123,696

[22] Filed: Jul. 28, 1998

[51] Int. Cl.$^7$ .......................... B01D 63/06; B01D 67/00; A61M 1/20

[52] U.S. Cl. ................................ 210/321.89; 210/321.61; 210/645; 96/10; 422/46; 422/48; 264/28; 264/258; 264/263; 264/311

[58] Field of Search ................................ 210/232, 321.71, 210/321.78, 321.79, 321.8, 321.88, 321.89, 323.2, 493.1, 493.2, 500.23, 645, 321.61; 264/28, 263, 311, 313, 258; 422/44–48; 96/8, 10

[56] References Cited

U.S. PATENT DOCUMENTS

| | | | |
|---|---|---|---|
| 3,442,002 | 5/1969 | Geary, Jr. et al. | 29/450 |
| 3,468,631 | 9/1969 | Raible et al. | 23/258.5 |
| 3,492,698 | 2/1970 | Geary, Jr. et al. | 18/26 |
| 3,615,238 | 10/1971 | Bentley et al. | 23/258.5 |
| 3,757,955 | 9/1973 | Leonard | 210/321 |
| 3,794,468 | 2/1974 | Leonard | 23/258.5 |
| 3,879,293 | 4/1975 | Wolf, Jr. et al. | 210/321 |
| 3,892,534 | 7/1975 | Leonard | 23/258.5 |
| 3,915,650 | 10/1975 | Talonn et al. | 23/258.5 |
| 3,927,980 | 12/1975 | Leonard | 23/258.5 |
| 3,929,414 | 12/1975 | Leonard | 23/258.5 |
| 4,061,470 | 12/1977 | Leonard | 23/258.5 |
| 4,138,460 | 2/1979 | Tigner | 264/159 |
| 4,151,088 | 4/1979 | Wolf, Jr. et al. | 210/180 |
| 4,211,597 | 7/1980 | Lipps et al. | 156/245 |
| 4,227,295 | 10/1980 | Bodnar et al. | 29/527.3 |
| 4,261,951 | 4/1981 | Milev | 422/46 |
| 4,289,623 | 9/1981 | Lee | 210/247 |
| 4,389,363 | 6/1983 | Molthop | 264/135 |

(List continued on next page.)

FOREIGN PATENT DOCUMENTS

| | | |
|---|---|---|
| 0 320 815 A2 | 6/1989 | European Pat. Off. . |
| 0 591 896 A2 | 4/1994 | European Pat. Off. . |
| 0 705 610 A1 | 4/1996 | European Pat. Off. . |
| WO 90/07943 | 7/1990 | WIPO . |
| WO 92/04060 | 3/1992 | WIPO . |
| WO 95/11709 | 5/1995 | WIPO . |
| WO 97/19742 | 6/1997 | WIPO . |

OTHER PUBLICATIONS

Instructions "Sarns™ SMO/IR Membrane Oxygenator with Integral Reservoir", Form 34–9996–9113–7 R/A, Undated.

Brochure "SMO/IR Sarns Membrane Oxygenator with Integral Reservoir", Form No. 78–8066–9350–9, 3M Health Care, Undated.

(List continued on next page.)

*Primary Examiner*—Joseph W. Drodge
*Attorney, Agent, or Firm*—Burns, Doane, Swecker & Mathis, LLP

[57] ABSTRACT

Tubular bundles are potted in a housing, such as in an oxygenator or a pheresis unit. Spacer material is placed into the housing to cover the first ends of the tubular elements. A layer of potting material is placed into the housing covering the spacer material, and then solidified in place to seal between each of the tubular elements and the housing. The spacer material is then removed from the housing to expose the first ends of the tubular elements. In the oxygenator, at least some of the tubes are gas exchange tubes having an interior lumen and a tube wall which is permeable for oxygen and carbon dioxide flow through the tube wall. The potting separates the housing into manifold chambers communicating with the interior of the tubes and a blood flow chamber sealed from the manifold chambers. Blood flows over the exterior surface of the tubes. Other tubes may be heat transfer tubes, such as for carrying a heat transfer fluid to control the temperature of the blood. Multiple pottings may be performed to provide separate sealed manifold chambers for each set of tubes.

30 Claims, 11 Drawing Sheets

U.S. PATENT DOCUMENTS

| | | | |
|---|---|---|---|
| 4,424,190 | 1/1984 | Mather, III et al. | 422/46 |
| 4,451,562 | 5/1984 | Elgas et al. | 435/2 |
| 4,469,659 | 9/1984 | Carson et al. | 422/46 |
| 4,496,458 | 1/1985 | Lee | 210/90 |
| 4,497,104 | 2/1985 | Fowles et al. | 29/419 |
| 4,517,090 | 5/1985 | Kersten et al. | 210/493.2 |
| 4,556,489 | 12/1985 | Diettrich, Jr. et al. | 210/321.3 |
| 4,559,999 | 12/1985 | Servas et al. | |
| 4,568,367 | 2/1986 | Gremel et al. | |
| 4,643,713 | 2/1987 | Viitala | 604/4 |
| 4,689,191 | 8/1987 | Beck et al. | 264/573 |
| 4,690,758 | 9/1987 | Leonard et al. | 210/247 |
| 4,715,953 | 12/1987 | Leonard | 210/321.8 |
| 4,735,775 | 4/1988 | Leonard et al. | 422/46 |
| 4,759,749 | 7/1988 | Verkaart | 604/113 |
| 4,791,054 | 12/1988 | Hamada et al. | 435/2 |
| 4,818,490 | 4/1989 | Carson et al. | 422/46 |
| 4,846,177 | 7/1989 | Leonard | 128/400 |
| 4,940,617 | 7/1990 | Baurmeister | 428/36.3 |
| 5,039,430 | 8/1991 | Corey, Jr. | 210/806 |
| 5,039,482 | 8/1991 | Panzani et al. | 422/46 |
| 5,043,140 | 8/1991 | Combs | 422/46 |
| 5,059,374 | 10/1991 | Krueger et al. | 204/156 |
| 5,112,480 | 5/1992 | Hukasawa | 210/188 |
| 5,152,964 | 10/1992 | Leonard | 422/48 |
| 5,192,478 | 3/1993 | Caskey | 264/139 |
| 5,192,499 | 3/1993 | Sakai et al. | 422/46 |
| 5,225,161 | 7/1993 | Mathewson et al. | 422/46 |
| 5,236,665 | 8/1993 | Mathewson et al. | 422/46 |
| 5,255,734 | 10/1993 | Leonard et al. | 165/96 |
| 5,266,265 | 11/1993 | Raible | 422/46 |
| 5,270,005 | 12/1993 | Raible | 422/46 |
| 5,270,007 | 12/1993 | Cosentino et al. | 422/46 |
| 5,382,407 | 1/1995 | Leonard | 422/48 |
| 5,422,057 | 6/1995 | Karbachsch et al. | 264/258 |
| 5,468,449 | 11/1995 | Sjogren et al. | 422/46 |
| 5,470,531 | 11/1995 | Sjogren et al. | 422/46 |
| 5,489,382 | 2/1996 | Tatebe et al. | 210/321.89 |
| 5,514,335 | 5/1996 | Leonard et al. | 422/46 |
| 5,531,848 | 7/1996 | Brinda et al. | 156/77 |
| 5,543,002 | 8/1996 | Brinda et al. | 156/77 |
| 5,578,267 | 11/1996 | Cosentino et al. | 422/46 |
| 5,639,373 | 6/1997 | Mahendran et al. | 210/500.23 |
| 5,747,138 | 5/1998 | Leonard | 428/113 |
| 5,753,173 | 5/1998 | Leonard et al. | 264/503 |
| 5,762,868 | 6/1998 | Leonard | 422/46 |

OTHER PUBLICATIONS

Brochure "SMO/INF Sarns Infant Membrane Oxygenator", Form No. 78–8066–9351–7, 3M Health Care, Undated.

Brochure "When you bring efficiency to the surface . . . you can lower the prime.", Form No. 16088004 Rev. B, Sarns, 3M Health Care, Undated.

Brochure "SMO/ICR Sarns Membrane Oxygenator with Integral Cardiotomy Reservoir", Form No. 78–8066–9349–1, 3M Health Care, Undated.

Instructions "Sarns® SMO/INF Infant Membrane Oxygenator", Form No. 16499401 R/D, 3M Health Care, Undated.

Galletti et al., "Artificial Lungs and Blood–Gas Exchange Devices", The Biomedical Engineering Handbook copy, 1995 by CRC Press, Inc., pp. 1879–1897.

Andrew L. Zydney, "Terapeutic Apheresis and Blood Fractionation", The Biomedical Engineering Handbook copy, 1995 by CRC Press, Inc., pp. 1936–1951.

POTTING OF TUBULAR BUNDLES IN HOUSING

CROSS-REFERENCE TO RELATED APPLICATION(S)

None.

BACKGROUND OF THE INVENTION

The present invention relates to potting of tubes in a housing to achieve a seal between the outsides of the tubes. The seal separates the housing into discrete chambers, with the tubes extending through the seal and in both chambers. In particular, the present invention may be used in oxygenators, sealing tubes which transmit gas or a heat transfer fluid from blood which passes over the outside surface of the tubes. The present invention may also be used in pheresis devices which separate a component from blood, also known as "plasmapheresis" or "apheresis" devices, or in a wide variety of other medical and technical devices.

Many modern devices for filtration, mass transfer and heat transfer in medical and other industries utilize a hollow fiber construction for efficient, compact operation. The tubular fibers are made from various materials such as polyolefins, cellulose, polysulfone, silicon rubber, polypropylene and others. The walls of these fibers may be either permeable or impermeable to the fluids carried therethrough, depending on the desired effect of the fluid transferred through the fiber with the fluid transferred over the fiber.

In particular, oxygenators for mass transfer between gas and blood may include hollow fibers disposed in a housing. The oxygenator functionally replaces the lung, adding oxygen and extracting carbon dioxide to transform venous blood into arterial blood. The primarily use for oxygenators is during cardiopulmonary bypass surgery.

The oxygenator may pump blood through the lumens of the hollow fibers while gas is exposed over the external surface of the capillary membranes. More preferably, gas flows through the lumens of the hollow fibers while blood is pumped over the external surface of the capillary membranes. This arrangement not only utilizes the larger outer surface area of the capillary tubes as gas transfer interface instead of the luminal surface, it also promotes blood mixing in a manner which enhances oxygen transport.

The external blood flow arrangement is most effective when the blood flows at generally right angles to the hollow fiber. The flowing blood successively encounters different fibers, and the transport of oxygen averaged over the periphery of each fiber is higher than with a parallel flow of blood. One structure to achieve a perpendicular external blood flow includes a blood inlet surrounded by gas flow fibers, with blood flowing radially outward through the fibers.

Blood pheresis, plasmapheresis or apheresis devices separate a specific component, such as plasma, a plasma component, white cells, platelets or red cells, from the remainder of the blood. Some medical procedures may include both "plasma exchange", in which the plasma is separated from the cellular components of the blood, and "plasma perfusion", in which the plasma is treated in a second filtration step to remove one or more specific components (such as a specific antibody, immune complex, globulin, toxin, protein, etc.) from the plasma. The treated blood may then be returned to the patient, often in combination with some type of replacement fluid.

Pheresis devices may use a hollow fiber construction to filter the blood as desired. Most commonly, any replacement component is allowed to mix into the blood during circulation through the patient. However, devices having a hollow fiber construction may also be used in some instances to place a replacement component back into the blood.

Oxygenators and/or pheresis devices must not induce trauma into the blood. The blood pressure and blood pressure differentials must not be too high, and the blood must be handled gently. The gas transfer membrane in an oxygenator must not allow the separation of plasma from the cellular components of the blood, which may cause plasma to seep through the fiber wall under pressure leading to a catastrophic decrease in membrane permeability. In contrast, the membrane in a pheresis unit may be intended to separate plasma from the cellular components of the blood.

In many applications, the blood must be maintained within a narrow temperature range, near body temperature. Often the surgeon/perfusionist may want careful control of the blood temperature, to "cool down" or "warm up" body functions of the patient. Oxygenators and/or pheresis units are therefore commonly coupled with heat transfer mechanisms to control blood temperature. For instance, heat transfer tubes having a controllable temperature may extend across the blood flow. One design includes using a heat transfer fluid such as water to transfer heat to and/or from the tubes. Similar to the gas exchange, heat transfer fluid may be channeled through hollow tubes which extend perpendicular to the blood flow, with blood flowing over the external surface of the heat transfer tubes. The tube walls for the heat transfer fluid should be thin and have a high heat conductivity, but should be impermeable to the heat transfer fluid and to blood.

Pheresis units and oxygenators in particular must be very reliable against leakage. Leakage of blood into the gas flow, into the heat transfer fluid flow, or into the separated blood component flow can clog the gas, heat transfer fluid or separated blood component flow and be detrimental to system performance, but does not immediately compromise the safety of the patient. Of more importance, direct flow of either oxygen (such as bubbles) or heat transfer fluid into the blood can catastrophically affect the patient. Leakage of water, for instance, into the blood can create severe hemolysis. The design of the oxygenator or pheresis device preferably allows complete, reliable separation between the blood flow path, the gas or separated component flow path, and (if present) the heat transfer fluid flow path.

The hollow fiber membranes in many current oxygenators are formed of microporous polypropylene. The fiber walls may have a wall thickness of 25 to 60 microns with a nominal pore size such as around 0.1 microns. With this wall thickness and pore size, the fiber walls are permeable to oxygen and carbon dioxide to allow free gas diffusion with the blood. The polypropylene is hydrophobic, and the fiber walls have a high enough surface tension to prevent plasma filtration at the moderate pressures in oxygenators.

Oxygenators must be competitively priced. Oxygenators must also be sterilized for each use. Because current oxygenator designs are not easily sterilized after use, oxygenators are disposable single-use items, which heightens the importance of cost. Pheresis devices and other medical fluid treatment devices have similar concerns. Microporous luminal fibers can be fabricated out of polypropylene on large scale and in defect free condition at a reasonable cost.

To form the blood treatment device, it is necessary to organize, hold and seal the luminal paths from the external blood flow path. One way to organize the hollow fibers is to weave the fibers into a mesh fabric, with the blood flow directed through the mesh fabric layer.

Seals are formed at the extremities of the hollow fibers, so the blood flow cannot come into direct contact with the luminal flow. For instance, the fibers may be "potted" in a sealing material to seal between the external surface of all of the fibers and the oxygenator housing. Typical potting compounds include acrylics, polyurethanes or epoxies.

Prior to placement of the potting compound, the bores of the fibers may be sealed or plugged in some manner to prevent potting compound entry. Luminal plugging may be performed by a heat or sonic seal. Luminal plugging may also be performed by a preliminary potting step, wherein the hollow fibers are potted to a shallow depth to form "potting caps" which plug the ends of the fibers. Potting caps are subject to leakage upon exposure to the primary potting compound, making controlling potting depth more difficult. The luminal plugging depth should be significantly less than the depth of the primary potting.

After the seals are formed between the hollow fibers, the hollow fibers are then manifolded or otherwise opened at their ends for luminal flow therethrough. For instance, after the potting compound has cured or otherwise solidified, a cutting operation may be used to cut off the plugged ends of the hollow fibers and a portion of the potting compound. The cutting typically requires very sharp cutters, usually with a lubricant of some type. The cutting operation exposes the inner bores of the fiber. The cutting process generates heat and chips which must be removed from the fibers and the housing. Excessive heat from cutting may reclose the lumen by smearing the potting compound over the cut surface.

In the typical potting and cutting operation, the manifolds and ports for the oxygenator are not added until after the cutting operation. Potting can occur directly in the housing, but then very special cutters and techniques must be used to cut both the hard material of the housing and the potted fibers. After the cutting operation, separate caps or manifolds must be added to the housing to provide entry and exit to the inner bores of the fibers. An additional seal must be made for the caps or manifolds, allowing for additional quality rejects or field failures.

As with any type of seal, the possibility of a leak occurring along the external surface of one or more fibers is a problem with potting. Leaks may occur due to poor fiber treatment, poor cleaning, air bubbles, or a defect in the potting compound. To minimize chances of leakage, the potting operation may be performed using a centrifuge, with centrifugal force pushing the potting compound outward to the ends of the fibers. Centrifugal potting helps to limit wicking of the potting compound along the fibers, eliminates bubbles, and more tightly packs the potting compound around the fibers.

BRIEF SUMMARY OF THE INVENTION

The present invention involves potting of a plurality of tubular elements, which is particularly applicable for oxygenators, pheresis devices and other fluid treatment devices. The tubular elements are placed in an aligned array within a housing, such as in a fiber bundle. A spacer material is placed into the housing to cover ends of the tubular elements. A layer of potting material is placed into the housing covering the spacer material, and then solidified in place to seal between each of the tubular elements and the housing. The spacer material is then removed from the housing to expose the ends of the tubular elements. If used to form an oxygenator, the tubes may be gas exchange tubes having an interior lumen and/or may be heat transfer tubes. Multiple pottings may be performed to provide separate manifold chambers for each set of tubes. Blood flows over the exterior surface of the tubes, sealed from the manifold chambers.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Figure 1:
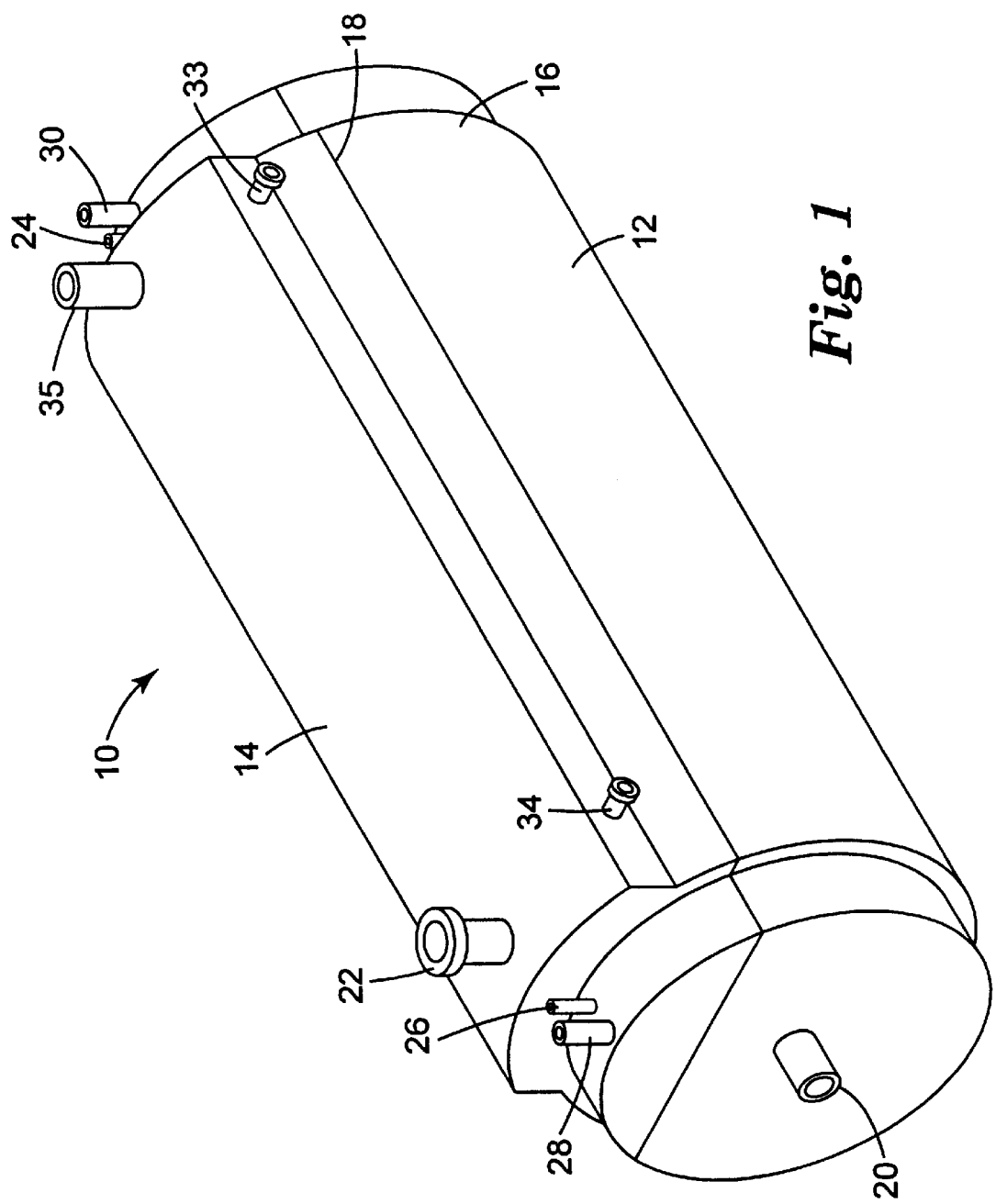
FIG. 1 shows a perspective view of an oxygenator in accordance with the present invention.
Figure 2:
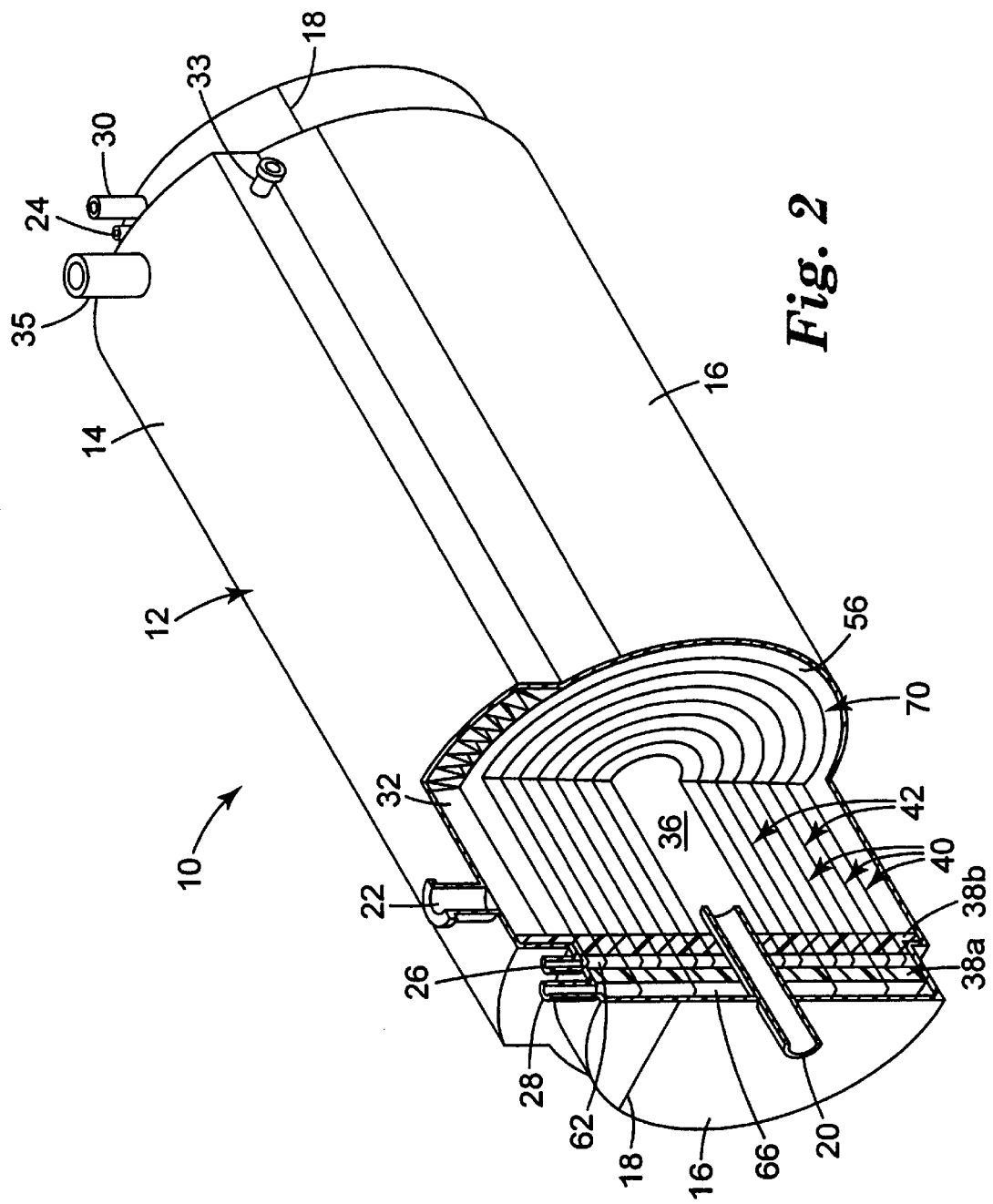
FIG. 2 shows a partial cross-sectional view cutaway from the oxygenator of FIG. 1.
Figure 4:
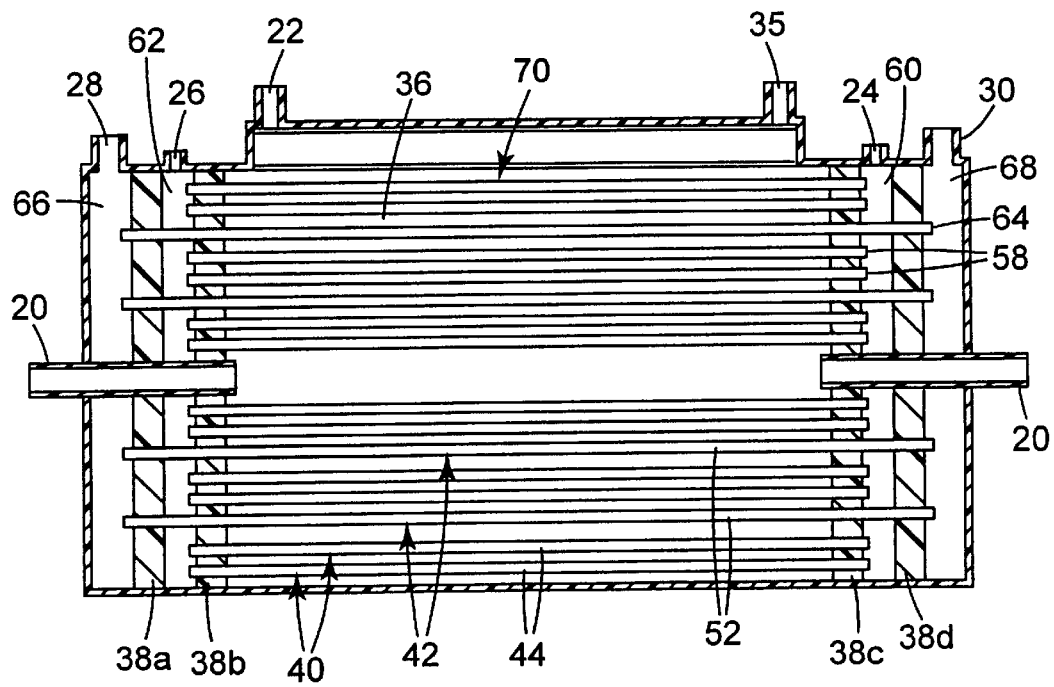
FIG. 4 shows a cross-sectional view of the oxygenator of FIG. 1.

FIGS. 1, 2 and 4 show an oxygenator 10 in accordance with the present invention. The oxygenator 10 includes a housing 12 formed of a rigid material, with a porting portion 14 and a casing portion 16. For instance, the housing 12 may be molded of polycarbonate, acrylic or polyester, and is preferably transparent to permit viewing of the interior of the oxygenator. The porting portion 14 and the casing portion 16 are sealed or molded together such as along a seal line 18, to together form a sealed chamber.

The housing 12 includes at least one blood inlet 20 for venous blood, a main blood outlet 22 for filtered arterial blood, a gas inlet 24 and a gas outlet 26. During use the gas inlet 24 will receive a flow of humidified oxygen, while the gas flow at the gas outlet 26 will generally be a mixture of carbon dioxide emitted from the blood, water vapor and oxygen.

The oxygenator 10 may provide for controllable heat transfer to and from the blood through a heat transfer fluid such as water. The housing 12 may accordingly include a water inlet 28 and a water outlet 30. Workers skilled in the art will appreciate that the blood temperature may be controlled through a variety of alternative equivalent ways. However, providing a separate system for heat transfer allows for a faster response time for temperature changes than, for instance, controlling the inlet temperature of the oxygen. Many other liquids could be equivalently used other than water, but temperature controlled water is inexpensive and readily available in an operating environment.

During use, the oxygenator 10 is preferably mounted with its longitudinal axis directed vertically, with the gas flow directed downward and the water flow directed upward. A downward gas flow helps to carry any condensation from the gas flow downward and out through the gas outlet 26. An upward water flow helps to evacuate air out of the water flow during priming of the water flow through the oxygenator 10. The terms "inlet" and "outlet", as used herein, merely indicate explanatory flow directions, and could easily be changed or reversed in any particular design or orientation.

In the preferred design as shown in FIGS. 2 and 4, a filter 32 is included immediately prior to the main blood outlet 22. The filter 32 is preferably woven of single filament or multiple filament polyester, such as with openings for blood flow of 20 to 40 $\mu$m, folded with accordion pleating. Because the polyester material is flexible, the filter 32 may also include a screen (not independently shown) to support the polyester portion of the filter. The screen for the filter 32 may be woven or extruded such as of polyester, polyethylene or polypropylene, and may have openings of about 120 $\mu$m. Many other types of filters can be equivalently used.

The housing may include outlets which bypass the filter 32, such as a vent 33 and a sampling port 34. The housing 12 may also include a blood recirculation port 35, which allows any accumulated gas which gathers downstream of the filter 32 to be bled out of the oxygenator 10.

The blood inlet 20 is preferably provided at the radial center of the housing 12. If desired, the housing 12 may include two blood inlets 20, either one of which may be plugged during use. The additional blood inlet 20 provides the perfusionist with flexibility in making the blood connection to the oxygenator 10. The blood inlet 20 extends axially to a blood oxygenation chamber 36 defined between two potting layers 38b, 38c. After traveling through the blood inlet 20, blood flows radially outward within the blood oxygenation chamber 36, where the blood passes through several gas exchange layers 40 which give oxygen to the blood and receive carbon dioxide from the blood. The blood also passes through several heat transfer layers 42.

Figure 3:
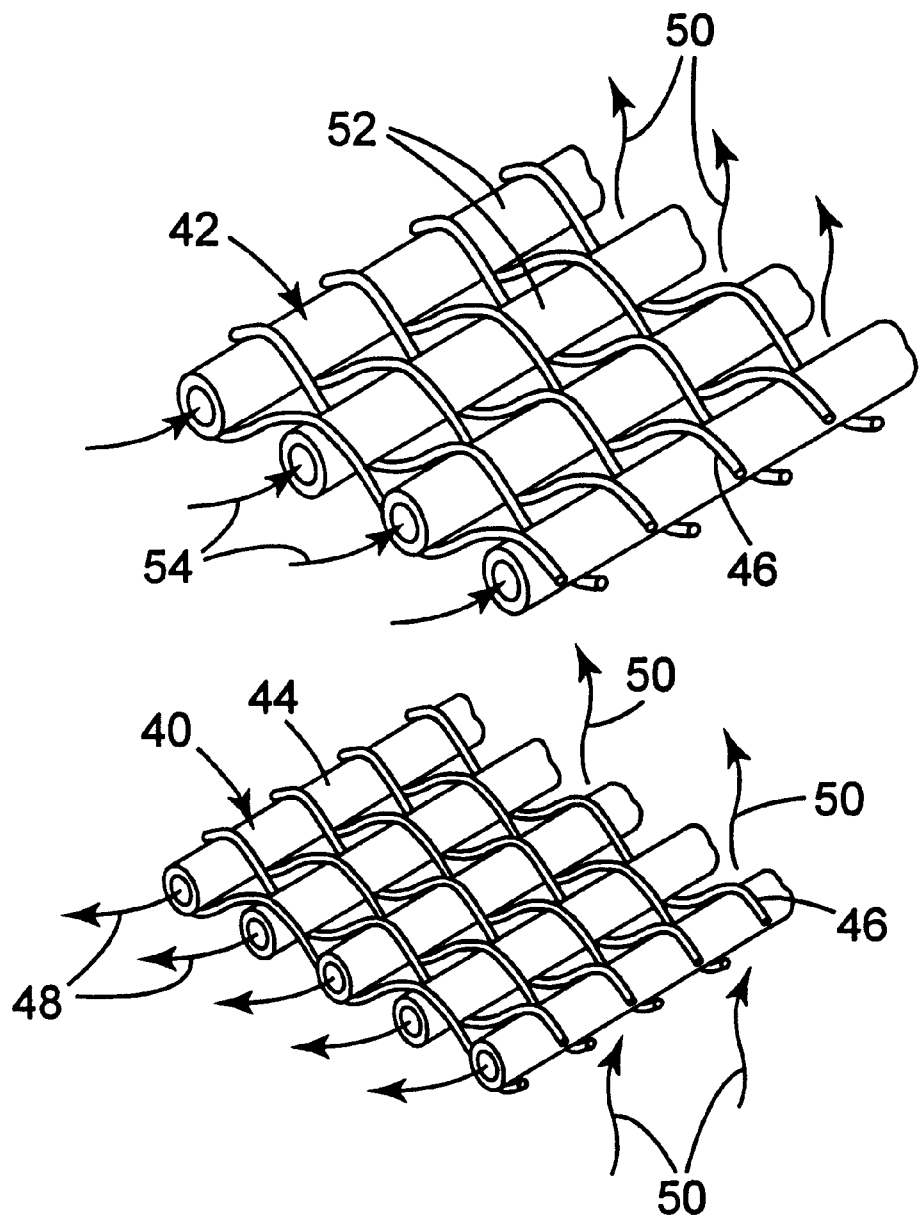
FIG. 3 shows a greatly enlarged perspective view of the gas exchange and heat transfer layers of the oxygenator of FIG. 1.

A greatly enlarged view of one gas exchange layer 40 and one heat transfer layer 42 is shown in FIG. 3. The gas exchange layer 40 is formed of numerous hollow fibers 44 suitable for oxygenation. The preferred material for the tubes 44 of the gas exchange layer 40 is microporous polypropylene, available from AKZO Nobel as "oxyphan". Typically these fibers 44 are 300 to 400 microns in outer diameter with a 25 to 60 micron wall thickness. The fibers may be spaced in the gas exchange layer 40 at about 10 to 20 fibers per cm. The hollow fibers 44 are woven with widely spaced cross strands 46 into layer 40 of mesh, so all the hollow fibers 44 are aligned into an array of generally parallel tubes 44. Gas flows through the lumens of the gas exchange layer 40 as shown by arrows 48. The radial direction of blood flow is shown by arrows 50, generally perpendicular to the gas exchange layer 40. The interaction between these flows causes oxygen to diffuse outward through the walls of the fibers 44 and into the blood, and causes carbon dioxide to simultaneously diffuse inward through the walls of the fibers 44 into the gas flow.

The heat transfer layer 42 is formed of numerous hollow fibers 52 suitable for heat exchange, such as a solid wall fiber made from polypropylene, polyester, or polyethersulfone. These fibers 52 typically have an outer diameter of 500 to 600 microns with wall thickness of 50 to 75 microns and are also available from AKZO Nobel. The heat exchange fibers 52 are impermeable to blood (including blood gasses) and impermeable to the heat transfer fluid such as water, so there is substantially no mass exchange through the fiber walls. Water flows through the lumens of the heat transfer layer 42 as shown by arrows 54. With this size of lumens for fibers 52 and a typical length for the heat transfer layer 42, the pressure loss for the water flow is about 200 mmHg. Heat transfer occurs through the walls of the fibers 52 to maintain the blood at a desired temperature, or to heat or cool the blood as desired. The heat transfer occurs over a wide surface area and therefor occurs directly throughout the blood flow, rather than requiring secondary heat transfer within the blood flow.

As opposed to control with a heat transfer fluid, the heat transfer could be equivalently provided with electrically controlled heating elements (not shown) disposed within the blood flow. The heat transfer tubes would not need to be hollow, but could be solid members which conduct heat axially or generate heat such as based on resistance to an electric current flowing therethrough.

Referring again to FIG. 2, a peripheral flow area 56 is provided for blood to gather after flowing through the layers 40, 42 and for blood to flow peripherally around the layers 40, 42 to the filter 32. The peripheral flow area 56 should be wide enough so the pressure drop due to the peripheral flow is minimal compared to the pressure drop through the layers 40, 42, assuring that blood flows radially outward in all directions relatively equally. However, the peripheral flow area 56 should not be so large as to require an excessive supply of "priming" blood for the oxygenator 10.

The axial flow of gas and water through the oxygenator 10 is further described with reference to FIG. 4, wherein the small tubes 44, 52 of the gas exchange layer 40 and the thermal transfer layer 42 are drawn to an enlarged scale to better show flow channels. The tubes 44 of the gas exchange layer 40 terminate in open ends 58. On one side, the open ends 58 are exposed within a gas inlet manifold chamber 60, and, on the opposite side, the open ends 58 are exposed within a gas outlet manifold chamber 62. Gas inlet manifold chamber 60 is defined by potting layers 38c and 38d, and gas outlet manifold chamber 62 is defined by potting layers 38a and 38b. Gas flows from the gas inlet 24 into the gas inlet manifold chamber 60 and thereafter through the tubes 44 of the gas exchange layers 40 and into the gas outlet manifold chamber 62 and out the gas outlet 26.

The gas exchange layer 40 extends fully through the blood oxygenation chamber 36, so there is no direct contact between the gas flow and the blood flow. The gas exchange layer 40 further extends fully through both potting layers 38b, 38c adjacent the blood oxygenation chamber 36, and at least partially into the gas manifold chambers 60, 62. The open ends 58 of the gas exchange layer 40 are at least about 0.005 inches from the surface of the potting layers 38b, 38c. For instance, the open ends 58 of the gas exchange layer 40 may be centered in the gas manifold chambers 60, 62. More preferably, the open ends 58 of the gas exchange layer 40 extend about 0.050 inches through the surface of the potting layers 38b, 38c. This distance ensures that open ends 58 avoid the possibility of blockage from the potting layers 38b, 38c, while still minimizing the length of the portion of the relatively expensive gas exchange mat 40 which does not make contact with the blood flow.

The tubes 52 of the heat transfer layer 42 terminate in open ends 64. On one side, the open ends 64 are exposed within a water inlet manifold chamber 66, and, on the opposite side, the open ends 64 are exposed within a water outlet manifold chamber 68. The water inlet manifold chamber 66 is are defined on the inside by the potting layer 38a and on the outside by the housing 12. The water outlet manifold chamber 68 is are defined on the inside by the potting layer 38d and on the outside by the housing 12. Water flows from the water inlet 28 into the water inlet manifold chamber 66 and thereafter through the tubes of the heat transfer layer 42 and into the water outlet manifold chamber 68 and out the water outlet 30.

The heat transfer layer 42 extends fully through the blood oxygenation chamber 36, so there is no contact between the water flow and the blood flow. The heat transfer layer 42 further extends fully through both potting layers 38b, 38c adjacent the blood oxygenation chamber 36, and fully through both gas manifold chambers 60, 62, so there is no contact between the water flow and the gas flow. The heat transfer layer 42 further extends fully through both potting layers 38a, 38d adjacent the water manifold chambers 66, 68 and at least partially into the water manifold chambers 66, 68. The open ends 64 of the heat transfer layer 42 are at least about 0.005 inches and more preferably about 0.050 from the surface of the potting layers 38a, 38d and into the water manifold chambers 66, 68.

The potting layers 38a, 38b, 38c, 38d seal between the water and/or gas tubes 44, 52 extending therethrough and the housing 12. Thus the blood oxygenation chamber 36 is completely separated from the gas manifold chambers 60, 62, all of which are completely separated from the water manifold chambers 66, 68.

The potting material can be, for instance, acrylic, polyurethane, epoxy or silicone. The preferred potting material is a light polyurethane potting compound such as available from Anderson Chemical Company, which comes in a two part liquid polymer/catalyst form which upon mixing rapidly solidifies by gelling and curing.

The potting layers 38 should be thick enough in the axial direction to make an intimate, lasting seal between the housing 12 (both at the shell and at the outside of the blood inlets 20) and the tubes 44 and/or 52. Each potting layer 38 should also be thick enough in the axial direction to withstand the pressure differential between its respective adjacent chambers (66 to 62, 62 to 36, 36 to 60, or 60 to 68). The blood pressures through the oxygenator 10 will typically be at about 200 to 300 mmHg, the gas pressure may be at about 10 to 20 cm $H_2O$ (7.4 to 14.8 mmHg), and the water pressure may be rated up to about 50 psi (2600 mmHg). The comparatively low gas pressure ensures that mass transfer through the fibers 44 will be by diffusion only and without bubbling. To withstand these pressure differentials and make an acceptable seal, the potting layers 38 may be about ¼ to ⅜ inches thick or thicker. The preferred potting layers 38, and particularly the potting layers 38b, 38c adjacent the blood oxygenation chamber 36, are as thin as strength and sealing requirements will allow, to minimize the length of the portion of the relatively expensive gas exchange mat 40 which does not make contact with the blood flow.

Workers skilled in the art will appreciate that many alternative oxygenator designs could be used other than the radial design shown. With a radial design as shown, the blood flow is generally at right angles to the luminal flow.

The blood, gas and water flow rates are determined by the pressure differential between the inlets and outlets, and can be primarily controlled by the surgeon/perfusionist by changing inlet pressures. Typical operating parameters for cardiopulmonary bypass in an adult include an oxygen transfer requirement of about 250 ml/min, a carbon dioxide elimination requirement of about 200 ml/min, and a blood rate of about 5 l/min. Mass transfer rates are determined by the partial pressures of oxygen and carbon dioxide in the blood and in the gas flow, and by the gas permeability and thickness of the luminal membrane. Venous blood typically has an oxygen partial pressure of about 40 mmHg and a carbon dioxide partial pressure of about 45 mmHg. The arterial blood at the main blood outlet 22 should have an oxygen partial pressure of about 100–300 mmHg and a carbon dioxide partial pressure of about 30–40 mmHg.

Figure 5:
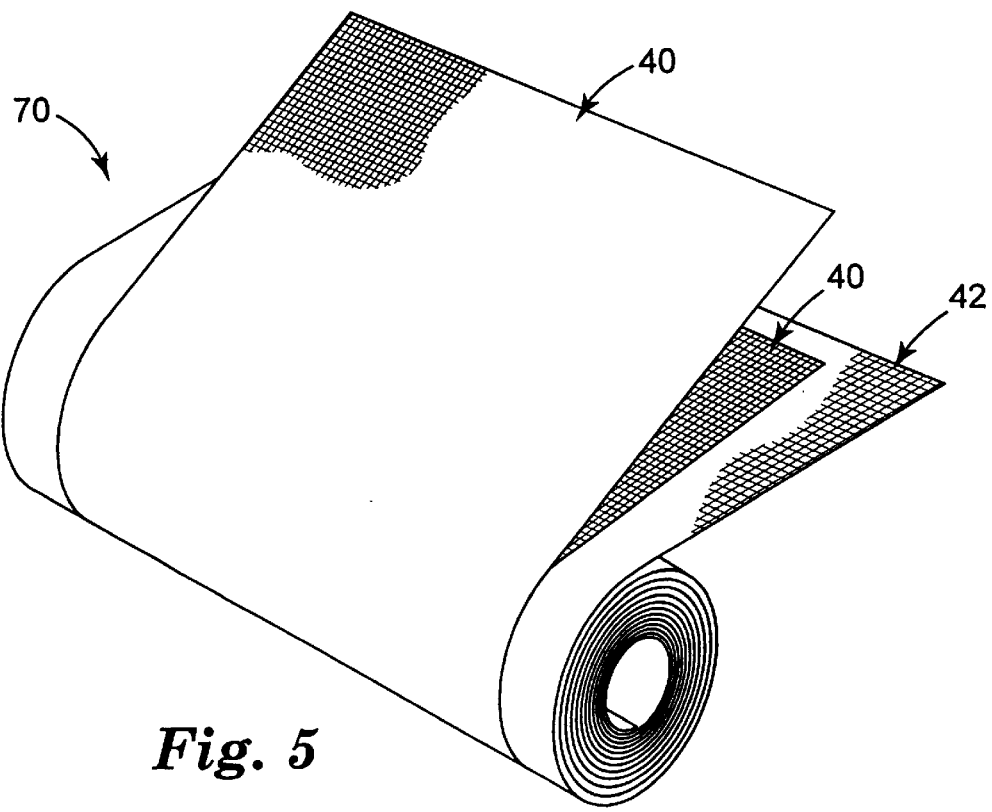
FIG. 5 shows a perspective view of the rolling of a fiber bundle for the oxygenator of FIG. 1.

FIGS. 5–11 show various steps in the process of manufacturing the oxygenator 10. As shown in FIG. 5, an initial step is the winding of the gas exchange fiber mat 40 and the heat transfer fiber mat 42 into a roll 70 known as a "bundle". The fiber mats 40, 42 are both flexible, with the hollow fibers 44, 52 oriented across the mats 40, 42, i.e., axially in the bundle 70. The hollow fibers 44, 52 of both mats 40, 42 are open at their ends 58, 64. The bundle 70 may be wound over a core (not shown), which may be either an eventual part of the device or be removed from the final bundle 70. The winding process may take place with the hollow fibers 44, 52 of adjacent layers 40, 42 at angles to prevent interdigitation or "nesting".

For simplicity, FIGS. 2, 4, 6 and 8–12 show only three turns or revolutions of two layers of gas exchange fiber mat 40, and two turns or revolutions of a single heat transfer fiber mat 42. To obtain the desired surface areas and spacing for the layers 40, 42, the layers 40, 42 may be spirally wound such as with about 15 to 20 revolutions or turns in the actual oxygenator product. With the preferred spacing between fibers 44, 52 and 15 to 20 turns of layers 40, 42, a typical pressure loss in the blood flow from inlet 20 to outlet 22 is on the order of 100 mmHg.

The ratio between the number of gas exchange fibers 44 and the number of heat transfer fibers 52 is selected based on the desired characteristics of the oxygenator 10. Typically the oxygenator 10 will include about 1.5 to 2.5 $m^2$ of surface area of gas exchange fibers 44 and about 0.5 to 1.0 $m^2$ of surface area of heat transfer fibers 52. Therefore a typically ratio might be two layers of gas exchange fiber mat 40 wound with one layer of heat exchanger fiber mat 42. The ratio between the number of gas exchange fibers 44 and the number of heat transfer fibers 52 can alternatively be adjusted by altering the spacing of the fibers 44, 52 in one or both mats 40, 42, although the void fraction requirement for proper blood flow through the layers 40, 42 poses limits on the fiber spacing.

The gas exchange fiber mat 40 has a different width (i.e., axial length in the bundle 70) than the heat transfer fiber mat 42. In the preferred arrangement, the heat transfer mat 42 is wider than the gas exchange mat 40. Alternatively, the gas exchange fiber mat 40 may be the same width as the heat transfer fiber mat 42, but be axially offset from the heat transfer fiber mat 42. In either event, the open ends 58 of the gas exchange fibers 44 generally define two nominal planes (i.e., an inlet plane and an outlet plane) which are separated from nominal planes defined by the open ends 64 of the heat transfer fibers 52.

Figure 6:
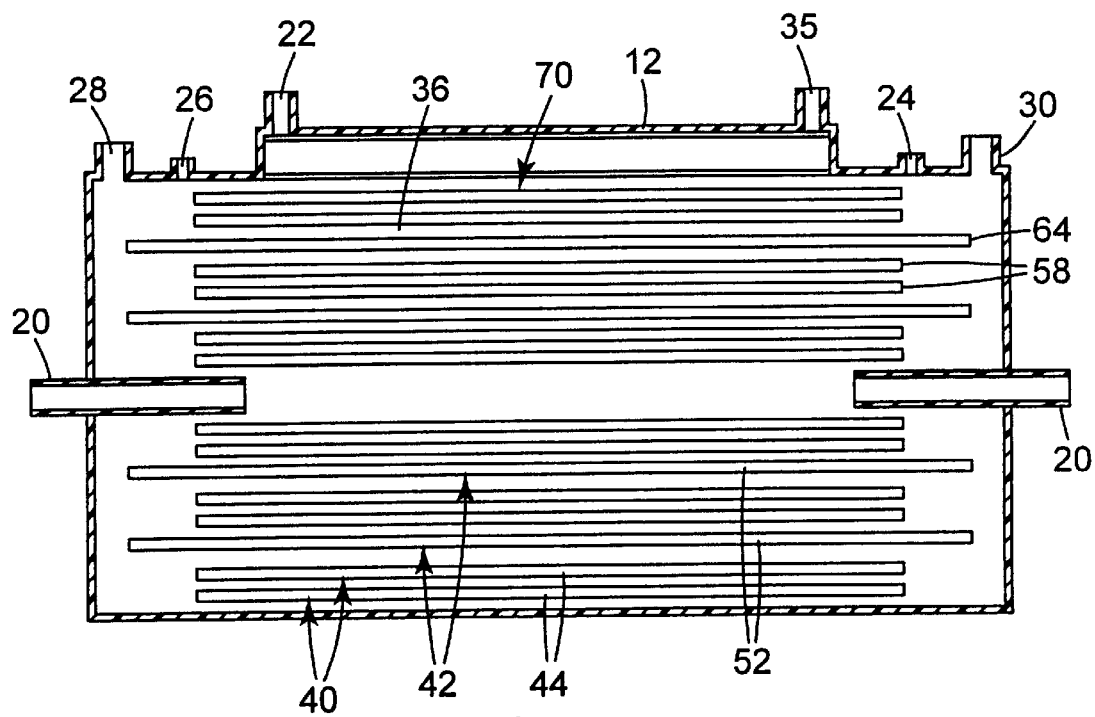
FIG. 6 shows a cross-sectional view of the oxygenator of FIG. 1 at an early step in the manufacturing process.

As shown in FIG. 6, the fiber bundle 70 is positioned within the housing 12. The housing used during the manufacturing step could alternatively be a temporary mold (not shown) having two portions which open and close around the fiber bundle 70, but preferably the housing 12 used during manufacturing is integral in the final oxygenator device 10. The porting portion 14 and the casing portion 16 of the housing 12 (shown in FIGS. 1 and 2) may then be sealed together around the fiber bundle 70. For instance, the housing 12 may be sealed by any of several known methods such as ultrasonics, adhesives, EMA bonding, or plastic welding.

Figure 7:
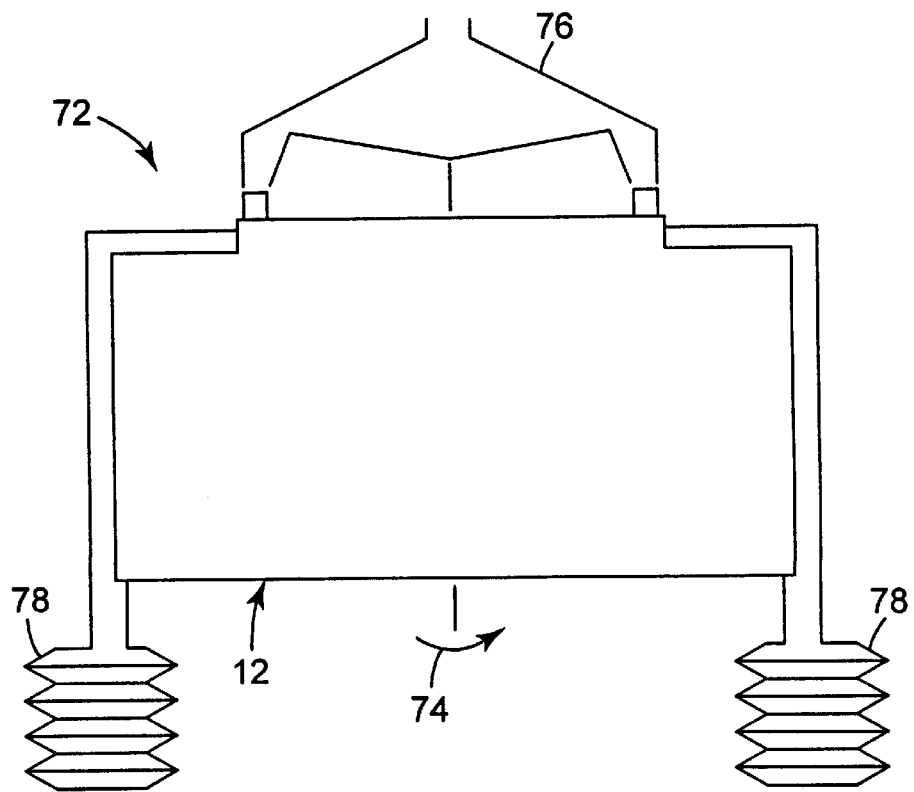
FIG. 7 shows the oxygenator of FIG. 6 mounted on a centrifuge manufacturing fixture.

As shown in FIG. 7, the housing 12 containing the fiber bundle 70 may then be placed in a centrifuge 72 (shown schematically) for rotation about a centrifuge axis 74. The centrifuge axis 74 is preferably transverse to the axial direction of the array of fibers 44, 52 in the bundle 70. The centrifuge axis 74 is preferably spaced in the center of the housing 12. Alternatively the housing 12 may be spun about one end of the housing 12. The centrifugal speed may be selected as needed, such as at about 800 rpm.

The centrifuge 72 preferably includes integral connections with a potting compound reservoir 76 and spacer material reservoirs 78 (shown schematically). Pumps (not shown) are included for both reservoirs 76, 78, which can pump a selected amount of material into and/or out of the housing 12 from each reservoir 76, 78. Alternatively, a bellows may used to bring the reservoirs to the proper level for each of the potting steps. An electric eye or other detection means feeds back a servo driving the bellows to finely adjust the position of the spacer material and/or potting compound. The reservoirs 76, 78 may include rotating seals to allow centrifuge rotation, or may be contained with the centrifuge spinning arm. In the preferred centrifuge fixture, connections between the housing 12 and both the potting compound reservoir 76 and the spacer material reservoirs 78 are made automatically.

Figure 8:
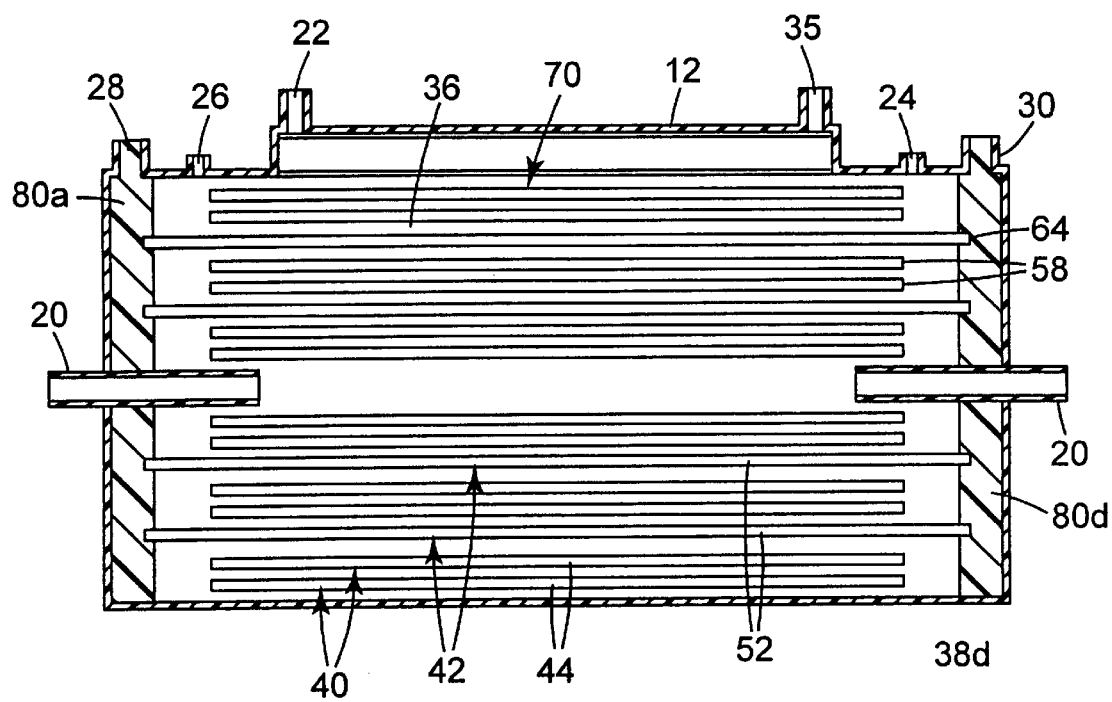
FIGS. 8–11 show the oxygenator of FIG. 7 at sequential steps in the preferred manufacturing process.

As represented in FIG. 8, spacer material 80a, 80d is introduced into the housing 12. The spacer material 80a, 80d and forced to the end walls of the housing 12 as shown due to centrifugal force. The amount of spacer material 80a, 80d introduced is selected to be deep enough to cover the water inlet 28, the water outlet 30 and the open ends 64 of the heat transfer tubes 52, but not so deep as to cover the open ends 58 of the gas exchange tubes 44. The exposed surface of the spacer material 80a, 80d thus forms nominal planes which intersect the heat transfer tubes 52 between the nominal plane of the open ends 64 and the nominal plane of the open ends 58. The term "nominal plane" as used herein does not require a completely planar surface, and centrifugal force causes the nominally planar surface of the spacer material 80a, 80d to adopt an arc about the axis of rotation 74. If desired, the nominal planes defined by the open ends 64 and the open ends 58 may follow a similar arc. The spacer material 80a may be added through the water inlet 28 and the spacer material 80d added through the water outlet 30, or the water inlet 28 and outlet 30 may be temporarily plugged and the spacer material 80a, 80d added through other ports. The amount of spacer material 80a added determines the volume of the water inlet manifold chamber 66, and the amount of spacer material 80d added determines the volume of the water outlet manifold chamber 68 of the oxygenator 10.

The preferred spacer material 80 is a heavy liquid such as perflurocarbon available from 3M of St. Paul, Minn. Perflurocarbons have a specific gravity between 1.7 and 1.9 and are chemically inert to most substances. Alternatively, the spacer material 80 may be introduced to the housing 12 as a fluid but then allowed to set or solidify, as by cooling, freezing, curing or gelling to form a solid substrate. If the spacer material 80 is a fluid, it will enter the bores of the fibers 52 as well as the space between the fibers 52 and the housing 12. The spacer material 80 could alternatively be a powder, such as a fine metal powder, which may be processed to flow as a fluid by a flow aid.

Figure 9:
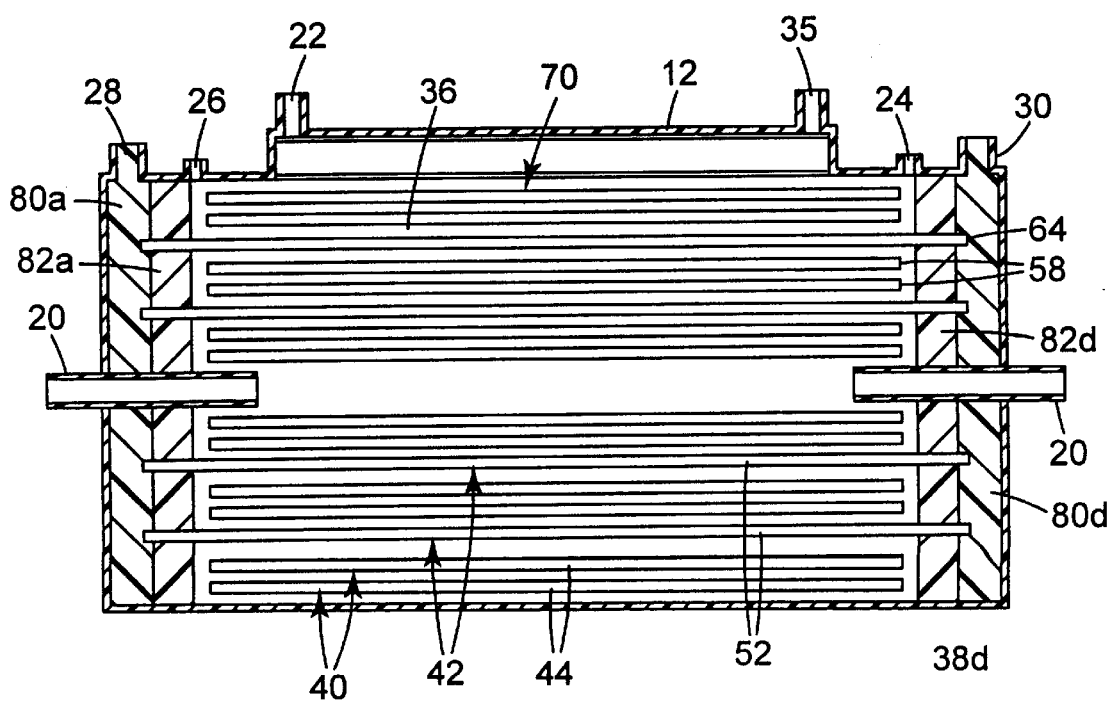

As represented in FIG. 9, potting compound 82a, 82d is introduced into the housing 12 preferably after the spacer material 80a, 80d is in place. The potting compound 82 may be added either through the spacer material 80a, 80d or through a separate port. The amounts of potting compound 82a, 82d introduced should be enough to provide a reliable seal between the housing 12 and the heat transfer tubes 52, but again be not so deep as to cover the open ends 58 of the gas exchange tubes 44. If the spacer material 80 is a powder, the powder should form a dense volume to preclude penetration by the potting compound 82 or limit penetration by the potting compound 82 to a few thousands of an inch.

The preferred potting compound 82 has a specific gravity between 1.1 and 1.2. This lighter compound 82a, 82d floats on the heavier spacer material 80a, 80d during centrifugation until it gels, cures or otherwise solidifies into the potting layers 38a, 38d. The solidification process may be from 3 to 15 minutes. If desired, the solidification can be accelerated by selecting an appropriate temperature/humidity for the solidification process, or by other methods known in the art such as exposure to ultraviolet or other radiation.

While the gas exchange fibers 44 do not enter the layers of potting compound 82a, 82d, the wrap of gas exchange fibers 44 serve to uniformly space the wraps of heat exchanger fibers 42 in the radial direction. The uniform spacing helps to allow an even flow of potting material 82a, 82d around the heat transfer tubes 52. The even flow allows air to pass out of this area as potting compound 82a, 82d is added, which is important to the formation of a reliable seal since, unlike the gas transfer fibers 44, the heat transfer fibers 52 are not microporous and do not allow for air removal through the tube walls.

While the preferred method is to place the spacer material 80a, 80d into the housing 12 prior to placing the potting compound 82a, 82d into the housing 12, the potting compound 82 may alternatively be placed into the housing 12 before the spacer material 80a, 80d. With proper selection of the density of the spacer material 80 and the potting compound 82, the spacer material 80a, 80d will displace the potting compound 82a, 82d inward to the desired location for potting layers 38a, 38d. Alternatively, both the potting compound 82a, 82d and the spacer material 80a, 80d may be placed into the housing 12 simultaneously, and then be allowed to separate in situ such as due to their differing densities.

Figure 10:
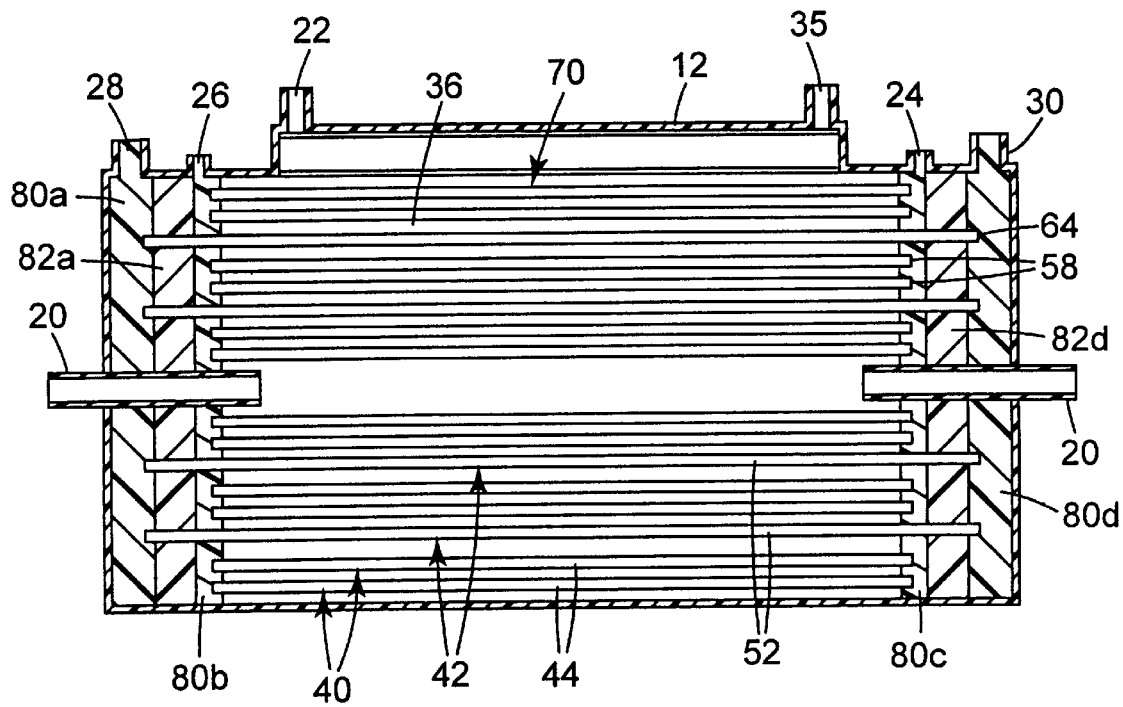

As represented in FIG. 10, second amounts of spacer material 80b, 80c are added to the housing 12 after the potting compound 82a, 82d solidifies into the potting layers 38a, 38d. The second amounts of spacer material 80b, 80c introduced are selected to be deep enough to cover the gas inlet 24, the gas outlet 26 and the open ends 58 of the gas exchange tubes 44. The exposed surface of the second spacer material 80b, 80c thus forms nominal planes which intersect the gas exchange tubes 44 and the heat transfer tubes 52. The spacer material 80c may be added through the gas inlet 24, and the spacer material 80b may be added through the gas outlet 26, or the gas inlet 24 and gas outlet 26 may be temporarily plugged and the spacer material 80b, 80c added through other ports. The amount of spacer material 80c added determines the volume of the gas inlet manifold chamber 60 and the amount of spacer material 80b added determines the volume of the gas outlet manifold chamber 62 of the final oxygenator product.

Figure 11:
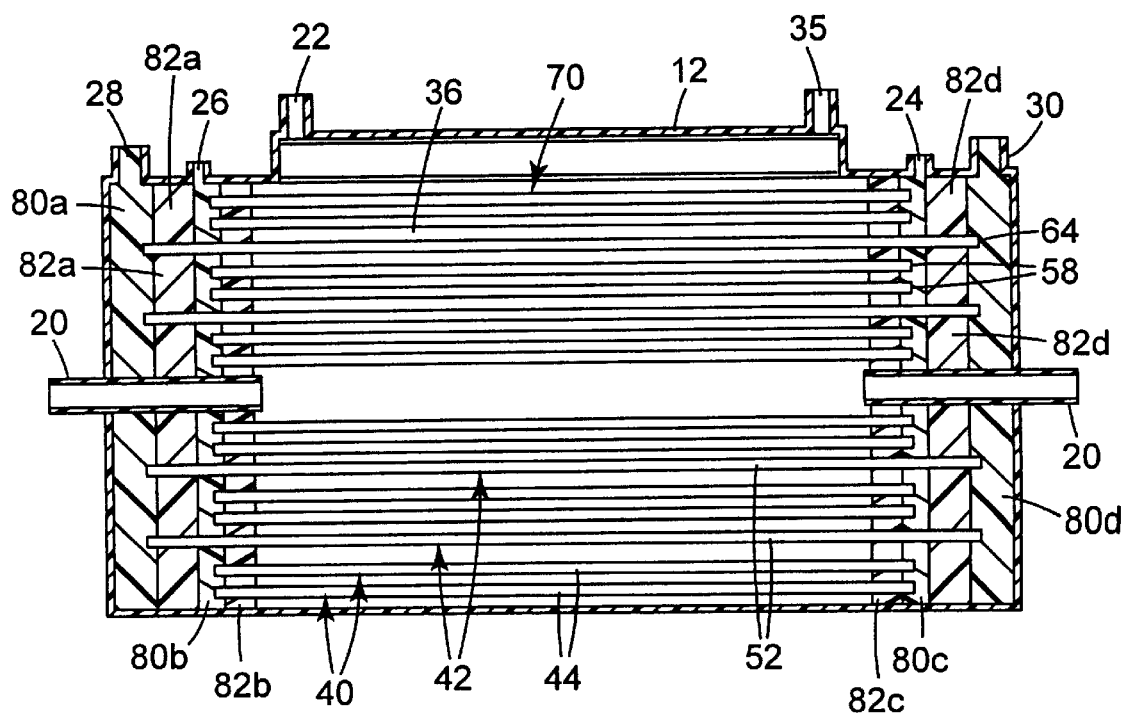

As represented in FIG. 11, second amounts of potting compound 82b, 82c are introduced into the housing 12 after the second spacer materials 80b, 80c are in place. The second amounts of potting compound 82b, 82c introduced should be enough to provide a reliable seal between the housing 12 and both the heat transfer tubes 52 and the gas exchange tubes 44, thereby defining the blood oxygenation chamber 36. Similar to the first potting compounds 82a, 82d, the second potting compounds 82b, 82c are allowed to solidify in place into the potting layers 38b, 38c.

After the overlying potting compounds 82b, 82c have solidified into the potting layers 38b, 38c, the spacer material 80b, 80c is removed from the housing 12. Preferably the spacer material 80a, 80d is also removed at this time, although it could have been removed earlier. The spacer material 80c that occupies the gas inlet manifold chamber 60 is removed through the gas inlet 24, the spacer material 80d that occupies the water outlet manifold chamber 68 is removed through the water outlet 30, etc. If the spacer material 80 is a high density liquid, it may be removed either with the aid of the pump or by centrifugal force. The centrifugal force also forces the spacer material 80 out of the fiber bores. If the spacer material 80 was a solidified fluid, it may be removed through melting or through dissolving in a solvent. A very small amount of fluid may be left which can evaporate into the air or be captured and condensed in a subsequent drying or leak checking operation.

After removal, the spacer material 80 is preferably returned back into the spacer material reservoir 78. If desired, a filtration or other purifying process may be incorporated in the spacer material return loop. The spacer material 80 is then ready to reuse for the next potting operation. Recycling of spacer material 80 preserves the spacer material 80 and eliminates any mess that merely dumping it would create.

The result of the potting process is perfect potting layers 38 surrounding and sealing the fibers 44, 52, with the open ends 58, 64 of the fibers 44, 52 extending through the respective potting layers 38. The surface of the potting layers 38 around the fibers 44, 52 is very smooth on both the inlet and outlet ends of both the gas exchange fibers 44 and the heat transfer fibers 52. The oxygenator 10 is easy to manufacture, very compact, and no cutting process is required. Rather than make two separate devices, the oxygenator/heat exchanger 10 is made at the same time in one process.

In the preferred process, the fibers 44, 52 are not only sealed to each other, but are also sealed to the housing 12 in a single step. Alternatively, the fibers 44, 52 may be potted in a mold (not shown), and then the fiber bundle 70 removed from the mold and sealed to the housing 12 as a separate step. Such an alternative method would allow potting of the fiber bundle 70 to occur at a different time or location than sealing the fiber bundle 70 to the housing 12, so the housing 12 of the final oxygenator 10 would not be required during potting.

Centrifugal potting helps to limit wicking of the potting compound 82 along the fibers 44, 52, eliminates bubbles, and more tightly packs the potting compound 82 around the fibers 44, 52. If a central axis 74 is used during rotation (rather than rotating about one end of the housing 12), centrifugal potting also allows potting of both ends of the fibers 44, 52 at the same time. The present invention may also be performed without a centrifuge and just using gravity. Gravity methods require supporting the housing 12 with the luminal fibers 44, 52 oriented vertically. The potting process is then performed through solidification of the potting compound 82, sealing the bottom ends of the fibers 44, 52 to the housing 12. The housing 12 is then inverted or flipped over so the solidified potting layers 38 are at the top, and the potting process is repeated on the bottom ends of the fibers 44, 52.

The present invention has advantages in utility and performance as well as in manufacture. With the present invention, manifolding of gas and heat transfer fluid is simple and direct, reducing both flow disturbance and pressure loss. The gas exchange fibers 44 and the heat transfer fibers 52 act in consort with each other in mixing the blood flow, aiding both the oxygenation and heat transfer processes.

During the rewarming process when the patient oxygen demand is increasing, the blood is gradually warmed as it passes through the fiber bundle 70. This means that the average blood temperature in the oxygenator 10 is below the exit temperature of the blood. With a lower average blood temperature, the partial pressure of oxygen in the blood is lower, resulting in a higher oxygen transfer to the blood. The process is reversed during blood cooling, with a higher average blood temperature in the oxygenator 10 than at exit, resulting in a lower oxygen transfer to the blood. However, during the cooling process, the oxygen demand of the patient is decreasing.

An additional beneficial effect is created due to the heat transfer fibers 52 extending through the gas inlet manifold chamber 60. Oxygen in the gas inlet manifold chamber 60 passes over the heat exchanger fibers before entering the gas exchange fibers 44. Any water condensation due to cooling of the oxygen occurs in the gas inlet manifold chamber 60 on the outside of the heat transfer fibers 52, rather than in the lumens of the gas exchange fibers 44. This helps exclude water condensation from the vapor crossing the microporous walls of the gas exchange fibers 44, which otherwise could accumulate and impair the oxygenation and carbon dioxide transfer through the gas exchange fiber walls.

A further beneficial result of the present invention is the ability of the oxygenator 10 to avoid catastrophic leaks into the blood flow. If either of the potting layers 38a, 38d adjacent the water manifold chambers 66, 68 leak, the leakage will be directed into the low pressure oxygen flow rather than into the blood flow. If either of the potting layers 38b, 38c adjacent the blood oxygenation chamber 36 leak, due to the relatively low pressure of the gas flow, the leakage will be of blood into the gas flow rather than of gas into the blood flow.

Figure 12:
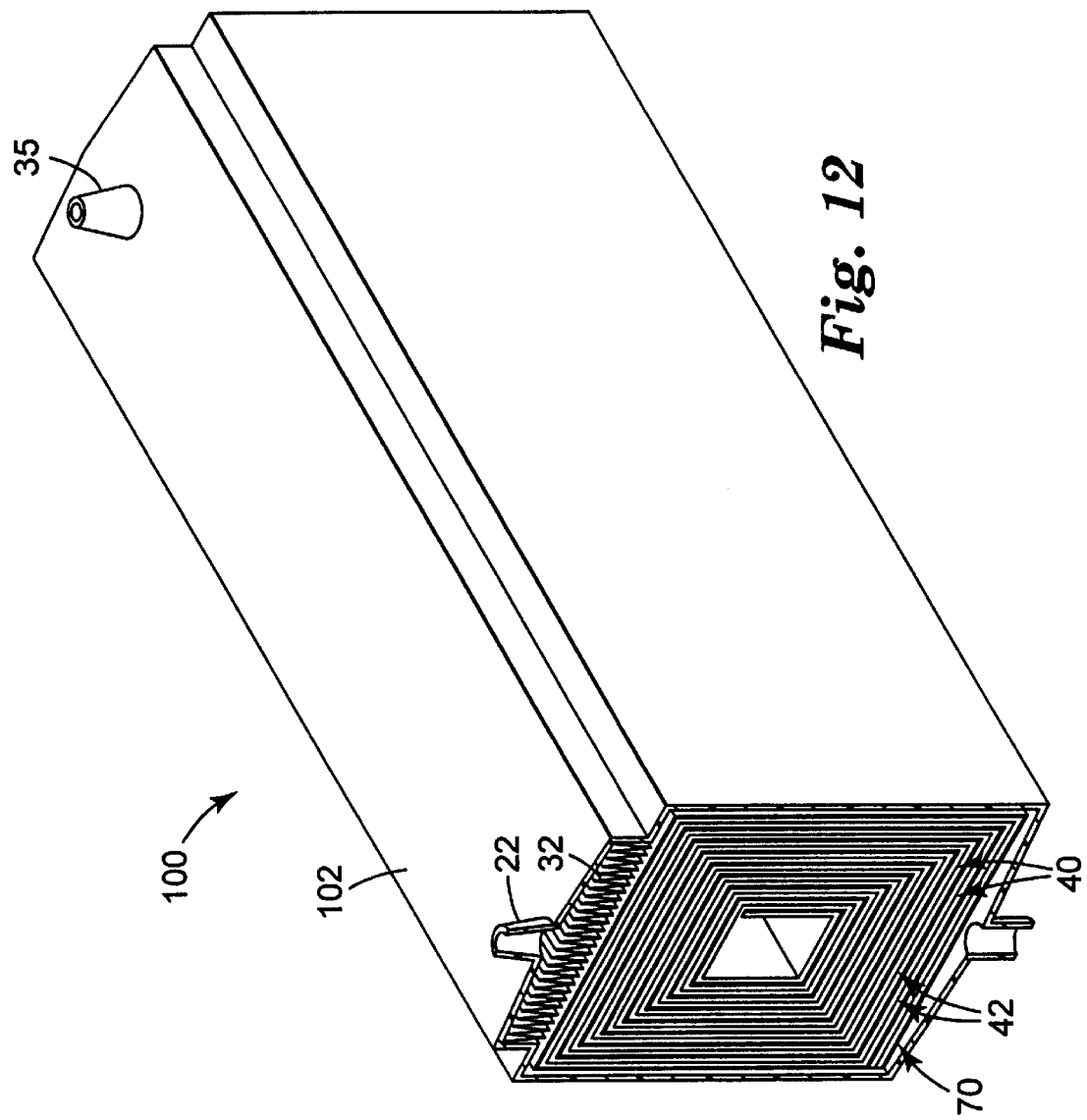
FIG. 12 shows a cross-sectional view of an alternative embodiment of an oxygenator in accordance with the present invention.

FIG. 12 shows one simple alternative embodiment of an oxygenator 100 in accordance with the present invention. The fiber bundle 70 of the oxygenator 100 is collapsed into a rectangular bundle by compressing it into a rectangular case 102. This oxygenator 100 allows a longer blood path with a different flow geometry. Many other, more different alternative embodiments can also be devised. Instead of or in conjunction with the heat transfer mechanism, other devices may be incorporated within the oxygenator such as filters, hemoconcentrators, or blood pheresis fibers. This may be done within the double pot described, or by incorporating additional potting layers to individually manifold the devices such as for hemoconcentrator or pheresis units.

Figure 13:
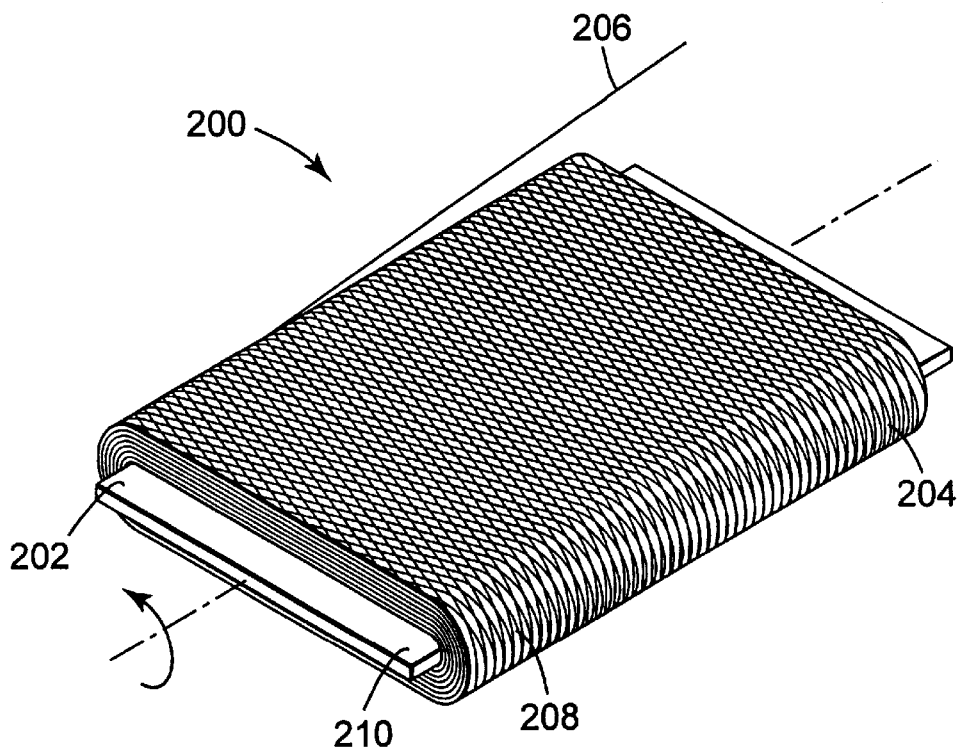
FIGS. 13–15 show sequential steps in a preferred manufacturing process for a blood pheresis device.
Figure 14:
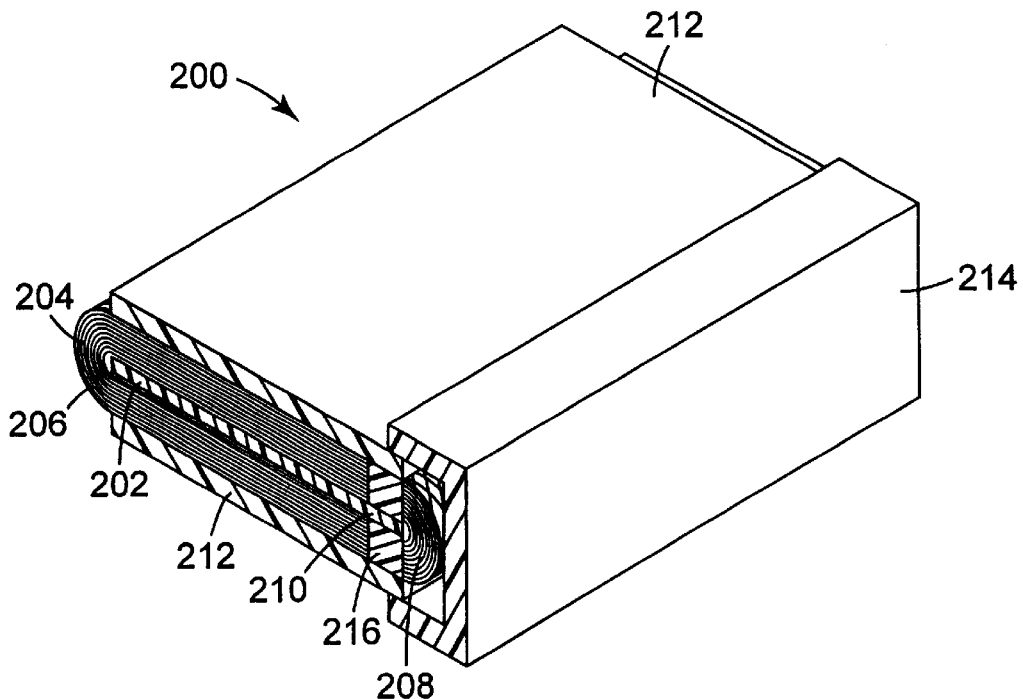
Figure 15:
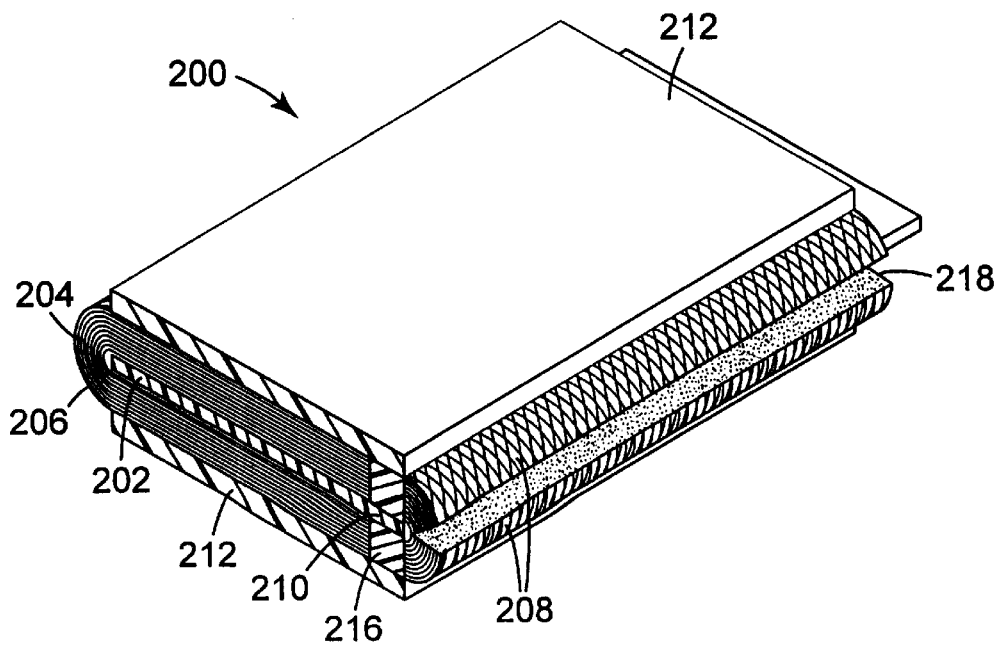

FIGS. 13–15 show application of the invention to an alternative device, a blood pheresis or plasmapheresis unit 200. The pheresis unit 200 begins with a flat core 202 formed of a rigid material such as polycarbonate. As shown in FIG. 13, a fiber bundle 204 is formed around the flat core 202 by winding a single fiber 206 around the core 202 in a spiral or helical pattern. Alternatively, multiple fibers may be simultaneously wound about the core 202, but a single fiber 206 produces a neat, easily manufactured array of fibers 204 with known winding techniques. As another alternative, a sheet of flexible fiber material (such as used in the oxygenator embodiment) may be rolled around the core 202, but with the tubular elements oriented circumferentially rather than longitudinally.

The core 202 does not serve a flow function in the final device, and may be omitted or removed after winding if desired. However, winding of the fiber(s) 206 is simplified by use of the central core 202. Wrapped around the core 202 as a single fiber 206, the ends 208 of the fibers 206 in the fiber bundle 204 are closed in a loop around the edge 210 of the core 202, with the lumen only open at the initial and final wrap of the single fiber 206.

The fiber 206 may be selected as desired for the function of the pheresis device. To separate plasma from the cellular components of the blood, a fiber called PLASMAPHAN available from AKZO Nobel of Germany may be used. RAYON fibers for separating plasma from the cellular components of the blood are also available from Mitsubishi of Japan. These fibers 206 preferably have an outer diameter of about 600 $\mu$m, and have permeable walls with openings which are about 10% of typical cellular component sizes. Other types of fibers may be used for separating other components out of the blood or out of the plasma. To minimize stretching of the fibers 206, they may be wound at a low winding tension such as about 10 to 20 grams. Workers skilled in the art will appreciate that the winding tension used may be selected based on the type of fiber used.

As known in the winding art, the fibers 206 may be wound at a significant angle to the longitudinal axis of the core 202 to provide a desired void fraction or percentage of open area through the fiber bundle 204. In the preferred pheresis unit 200, the fiber 206 is wound to a void fraction of about 50%. The void fraction may selected as desire for the particular fluid and components to be filtered.

After wrapping the fiber 206 into this array 204 about the core 202, the fiber array 204 is positioned relative to two plates 212 and an end cap 214 as shown in FIG. 14. The plates 212 may be a temporary housing used only during the manufacturing process, or more preferably serve as the housing for the final device. The housing 212 is preferably formed of a transparent polycarbonate, and the end cap 214 may be formed of a rigid polypropylene. The assembly shown in FIGS. 14–15 is shown in partial cross-section for clarity, without showing sides of the housing 212 or end cap 214 or inlet or outlet ports.

After assembling with plates 212 and the end cap 214, potting compound 216 is placed with the method of the present invention as described for the previous embodiments. The pheresis device 200 is mounted in a centrifuge, with the longitudinal axis oriented vertically and facing outwards. As the centrifuge spins, positioning material is added to the end cap 214 until it reaches and covers the ends 208 of the fibers 206 and preferably just touches the edge 210 of the core 202. Potting compound 216 is then added to some depth to embed around the fibers 206. During this process, the core 202 may be used as a marker for proper depth of the positioning material and the potting compound 216. The potting compound 216 seals between each of the fibers 206, and preferably also seals between the fiber array 204 and the core 202 and the plates 212. The positioning material is removed after the potting compound 216 solidifies, and the end cap 214 may also be removed.

As shown in FIG. 15, the ends 208 of the fibers 206 may then be cut with a single slit 218 oriented in the longitudinal direction of the device 200. The position of each of the fibers 206 in the array 204 is generally maintained during and after cutting by the potting layer 216. The slit 218 exposes the inner lumen at the ends 208 of the fibers 206. The tension during wrapping places a small wound in stress in the fibers 206, which is relieved by cutting. The open ends 208 therefore tend to spring back after cutting, so the slit 218 widens somewhat into a V-shaped.

After cutting, the fiber array 204 may be placed in a final end cap (not shown) and sealed such as with a gasket (not shown), to provide a chamber for plasma collection which is sealed by the potting layer 216 from the blood flow between the plates 212. Additional manifolds (not shown) may be attached, or the ends of the plates 212 may have appropriate manifolds (not shown).

During use of the pheresis device 200, blood is pumped through the fiber array 204 in the longitudinal direction, such as with an inlet pressure of 200 mm Hg. Under the pressure of the blood flow, plasma in contact with the fibers 206 seeps through the walls and into the lumens of the fibers 206. Under the pressure of the blood flow, plasma is pushed in the transverse direction of the device 200 within the fibers 206, beyond the potting layer 216, and out the open ends 208 of the fibers 206. The cellular components of the blood cannot pass through the fiber walls, and consequently are driven in the longitudinal direction through the void space in the fiber array 204 and out of the pheresis unit 200. The "hematocrit" of the blood, or the ratio of the cellular components to total volume, which may be about 10% upon entry into the pheresis device 200, may be increased to about 50% due to the significant amount of plasma removed.

The method of the present invention avoids having to cut through the potting compound 216, which much might be very rigid. Instead, the method the present invention requires that only the fibers 206 be cut. If desired, the same procedure may be performed at the opposing end of the fibers 206 and the opposing edge of the core 202, such that the fibers 206 are potted and open at both sides of the pheresis unit 200.

Figure 16:
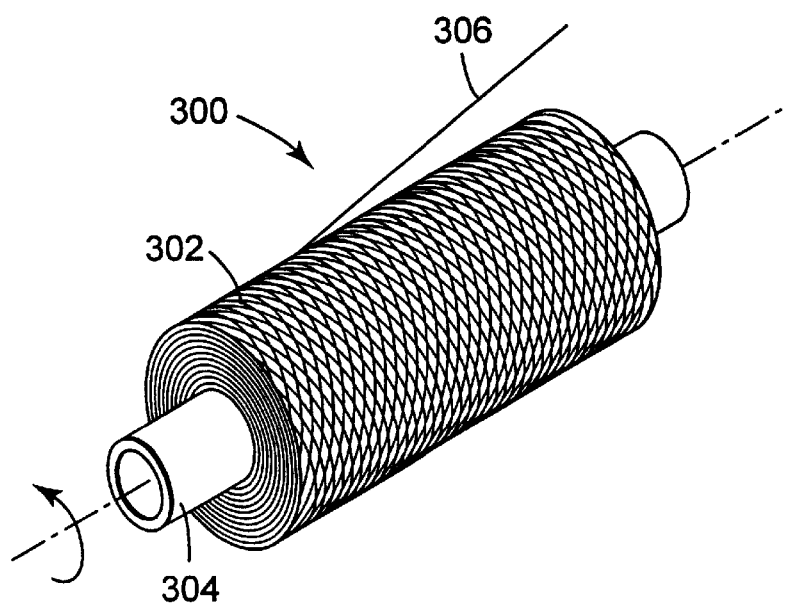
FIGS. 16–18 show sequential steps in a preferred manufacturing process for an alternative pheresis device.
Figure 17:
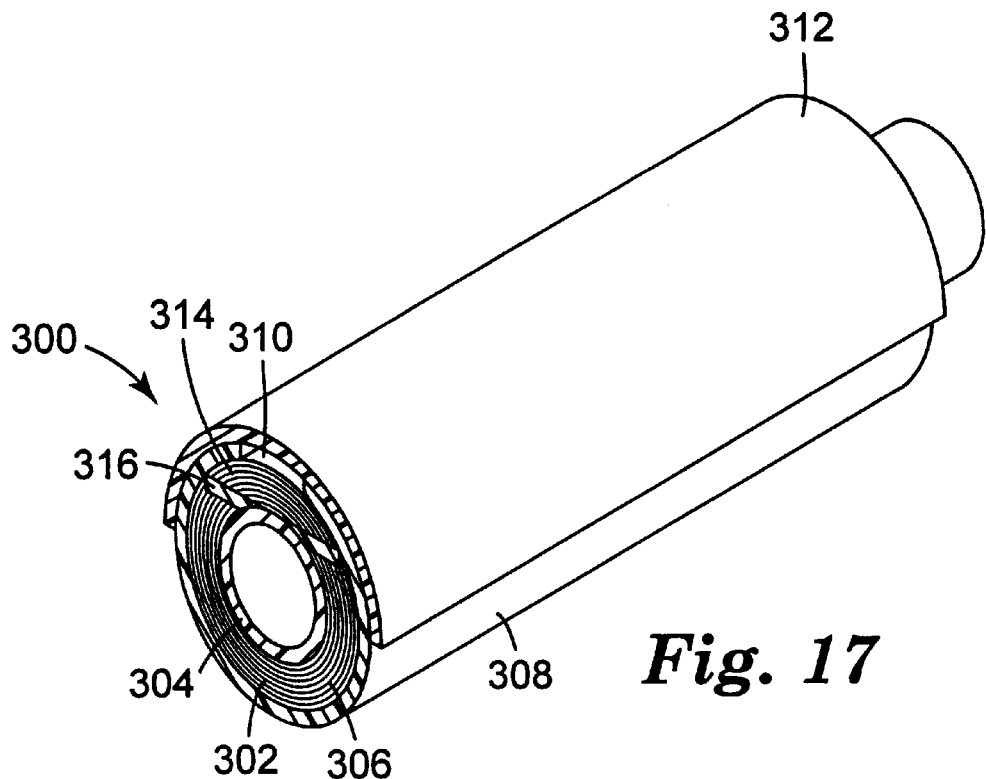
Figure 18:
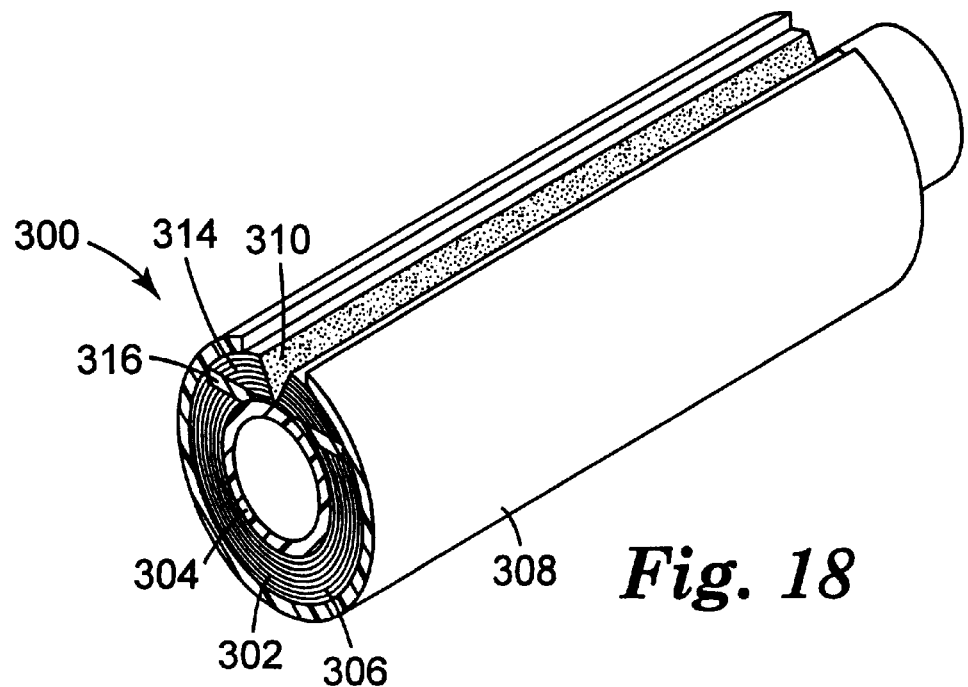

FIGS. 16–18 show an alternative blood treatment unit 300 similar to that shown in U.S. Pat. No. 4,715,953 entitled HOLLOW FIBER SEPARATION DEVICE MANIFOLD, incorporated herein by reference. In this case, as shown in FIG. 16, a fiber bundle 302 is wrapped around a circular or cylindrical core 304. The cylindrical core 304 helps to minimize bending stresses in the fibers 306. After wrapping, the circular fiber array 302 is placed in a case 308 with an open longitudinal slit 310 as shown in FIG. 17. A temporary cap 312 is placed over the slit 310. With the cap 312 in place, the device 300 is mounted vertically in the centrifuge with the cap 312 directed outward. As the centerfuge spins, positioning liquid is added to the cap 312 until it covers the ends 314 of the fibers 306 adjacent the open slit 310 and touches the inner core 304. Potting compound 316 is then added to a depth sufficient to seal the fibers 306 against the intended pressure.

The temporary cap 312 and positioning liquid are then removed as shown in FIG. 18, and the ends 314 of the fibers 306 are cut to expose the inner bores. A single or double manifold (not shown) can then be added to direct flow, or a hardware device with manifolds (not shown) can be gasketed or sealed to the case 308.

In use, the blood flow in the unit 300 may be longitudinal and on the outside of the core 304. Alternatively, the unit 300 may be modified to permit radial flow such as in the oxygenator embodiment. For radial flow, the size of the housing 308 should be increased relative to the outer diameter of the fiber bundle 302 to provide a collection chamber (not shown) outside the fiber bundle 302, and the core 304 may be formed at least in part of a mesh or otherwise include sizeable openings (not shown) on the side away from the potting compound 316, so blood can flow radially through the core 304.

Although the present invention has been described with reference to preferred embodiments, workers skilled in the art will recognize that changes may be made in form and detail without departing from the spirit and scope of the invention.

While an oxygenator and pheresis devices were used to discuss the method and apparatus of the present invention, the present invention is also applicable to many other devices wherein a seal must be made to define two chambers with an array to tube elements extending through the seal. Depending upon the application for the device, the tube elements may selectively transfer mass and/or heat to the fluid flow over the tube elements (as shown in the described oxygenator and pheresis devices), or may be used as a propagation medium for intimate transfer to the fluid flow, such as in the selective transfer of radiation (visible light, infrared, ultra-violet, x-ray, microwave, etc.), electricity, vibration such as sound, etc. to the fluid flow.

For instance, the present invention is applicable to medical devices such as dialyzers, hemoconcentrators, membrane cell washers, hemo filtration devices and fluid cell power supplies. The present invention is also applicable to non-medical devices such as chemical heat exchangers, reverse osmosis cells for desalinating water, devices for adding or removing gasses from fluids such as for water treatment or carbonation adjustment, and other devices, and particularly other devices with combined or multiple flow functions.

What is claimed is:

1. A method for potting, a plurality of tubular elements within a housing, the method comprising:

providing a housing;

placing a plurality of tubular elements in an aligned array within the housing, each of the tubular elements having a first end at a first side of the aligned array;

placing spacer material into the housing to cover the first ends of the tubular elements, the spacer material being fluid at the time of placing, the spacer material forming a first surface intersecting each of the tubular elements;

placing a first layer of potting material into the housing and covering the first surface of the spacer material, the first layer of potting material being fluid at the time of placing; solidifying the first layer of potting material to seal between each of the tubular elements; and substantially removing the spacer material from the housing to thereby define a first fluid manifold within the housing and to expose the first ends of the tubular elements, the first ends of the tubular elements being in fluid communication with the first fluid manifold.

2. The method of claim 1, wherein the tubular elements have walls defining a lumen for flow therethrough, and wherein the walls are permeable to oxygen and carbon dioxide.

3. The method of potting of claim 1, wherein the tubular elements have a second end at a second side of the aligned array opposite the first side, the second end being in fluid communication with the first end through lumen of each of the tubular elements, the method further comprising:

placing spacer material into the housing to cover the second ends of the tubular elements, the spacer material being fluid at the time of placing, the spacer material forming a second surface intersecting each of the tubular elements and spaced from the first surface;

placing a second layer of potting material into the housing and covering the second surface of the spacer material, the second layer of potting material being fluid at the time of placing;

solidifying the second layer of potting material to seal between each of the tubular elements; and substantially removing the spacer material to expose the second ends of the tubular elements.

4. The method of claim 3, wherein the solidifying of the first layer of potting material occurs simultaneously with the solidifying of the second layer of potting material.

5. The method of claim 4, further comprising spinning the housing with tubular elements therein in a centrifuge during the solidifying steps, with centrifugal force placing the first surface in a different nominal plane than the second surface.

6. The method of claim 1, wherein the potting material has a lesser density than the spacer material causing the potting material to separate from the spacer material.

7. The method of claim 1, further comprising:

solidifying the spacer material prior to placing of the first layer of potting material.

8. The method of claim 7, wherein the solidifying of the spacer material is by freezing, and further comprising:

melting the spacer material after solidifying of the first layer of potting material.

9. The method of claim 7, wherein the solidifying of the spacer material is by gelling, and further comprising:

dissolving the spacer material in a solvent after solidifying of the first layer of potting material.

10. The method of claim 1, wherein the spacer material is a perflurocarbon.

11. The method of claim 1, further comprising:

collecting the spacer material after removal; and reusing the spacer material in subsequent potting.

12. The method of claim 1, wherein the spacer material is a powder.

13. The method of claim 1, wherein the plurality of tubular elements in an aligned array are provided in a flexible mat, and further comprising the act of rolling the mat into a radial configuration prior to placing the mat within the housing.

14. The method of claim 1, wherein the solidifying of the first layer of potting material is by curing.

15. The method of claim 1, further comprising:

placing a second plurality of tubular elements in a second aligned array within the housing, each of the second plurality tubular elements having an end offset from the first ends;

placing spacer material into the housing to cover the ends of the second plurality of tubular elements, the spacer material being fluid at the time of placing, the spacer material forming a second surface intersecting each of the second plurality of tubular elements;

placing a second layer of potting material into the housing and covering the second surface of the spacer material, the second layer of potting material being fluid at the time of placing, the second layer of potting material being spaced from the first layer of potting material;

solidifying the second layer of potting material to seal between each of second plurality of tubular elements; and substantially removing the spacer material from the housing to expose the ends of the second plurality of tubular elements, and such that the ends of the second plurality of tubular elements are sealed from fluid communication with the first ends.

16. The method of claim 1, wherein the housing is a housing of a final device, and wherein the solidifying act also seals between the tubular elements and the housing.

17. The method of claim 1, wherein the tubular elements each have a wall defining a lumen for flow therethrough, and further comprising:
cutting the plurality of tubular elements at the first ends to expose the lumens.

18. The method of claim 1, wherein each of the plurality of tubular elements have a wall defining a lumen for flow therethrough, and wherein the walls of the tubular elements are permeable to at least one but not all components of blood.

19. A device for use in treating a fluid flow, the device comprising:
a housing having a fluid inlet and a fluid outlet;
a plurality of tubular elements in an array within the housing, each of the tubular elements having a first end and a second end opposite the first end;
a layer of potting material sealing between each of the tubular elements and supporting the tubular elements in a generally fixed position, the layer of potting material having a first surface and a second surface each intersecting the plurality of tubular elements such that each of the first ends protrudes through the first surface and each of the second ends protrudes through the second surface, the layer of potting material defining a sealed boundary of a fluid flow channel from the fluid inlet across the plurality of tubular elements to the fluid outlet.

20. The device of claim 19, wherein the plurality of tubular elements are connected to each other in a flexible sheet material.

21. The device of claim 19, wherein each of the plurality of tubular elements have a wall defining a lumen for flow therethrough.

22. The device of claim 21 as a filter, wherein the walls of the tubular elements are permeable to at least one but not all components of the fluid flow, and wherein the housing comprises a port in fluid communication with the lumens of the tubular elements for flow of a separated component of the fluid flow.

23. The device of claim 21 as a pheresis unit, wherein the fluid flow is blood flow, and wherein the walls of the tubular elements are permeable to at least one but not all components of blood.

24. A medical device for controlled transfer between a first fluid flow and a second fluid flow, the medical device comprising:
a housing having a first fluid inlet, a first fluid outlet, a second fluid inlet and a second fluid outlet;
a plurality of first tubular elements in an aligned array within the housing, each of the first tubular elements having a lumen for flow between the first fluid inlet and the first fluid outlet, each of the first tubular elements having walls which permit controlled transfer therethrough, each of the first tubular elements having a first open end toward the first fluid inlet and a second open end toward the first fluid outlet;
a first layer of potting material sealing between each of the first tubular elements, each of the first open ends protruding through the first layer; and
a second layer of potting material sealing between each of the first tubular elements, the second layer spaced from the first layer, with a second fluid flow channel defined between the first layer and the second layer, the second fluid flow channel extending from the second fluid inlet across the first tubular elements to the second fluid outlet, each of the second open ends protruding through the second layer.

25. The medical device of claim 24 as an oxygenator, wherein the first fluid is gas and the second fluid is blood, and wherein the walls of the first tubular elements are permeable to oxygen and carbon dioxide.

26. The oxygenator of claim 25, wherein the housing has a temperature regulation fluid inlet and a temperature regulation fluid outlet, and further comprising:
a plurality of second tubular elements in an aligned array within the housing, each of the second tubular elements having a lumen for flow between the temperature regulation fluid inlet and the temperature regulation fluid outlet, each of the second tubular elements having a first open end toward the temperature regulation fluid inlet and a second open end toward the temperature regulation fluid outlet;
a third layer of potting material sealing between each of the second tubular elements, the third layer spaced from the first layer and the second layer, each of the first open ends of the second tubular elements protruding through the third layer; and
a fourth layer of potting material sealing between each of the second tubular elements, the second layer spaced from the first layer, the second layer and the third layer, each of the second open ends of the second tubular elements protruding through the second layer,
wherein a temperature regulation fluid channel extends between the third layer and the fourth layer from the temperature regulation fluid inlet across the second tubular elements to the temperature regulation fluid outlet.

27. The oxygenator of claim 26, wherein the plurality of second tubular elements extend through the first layer and the second layer, and such that a gas inlet flow channel is defined from the first fluid inlet between the first layer and the third layer to the first open ends of the first tubular elements, and a gas outlet flow channel is defined from the second open ends of the first tubular elements between the second layer and the fourth layer to the second fluid outlet.

28. The oxygenator of claim 26, wherein the plurality of first tubular elements are provided in a flexible first mat and the plurality of second tubular elements are provided in a flexible second mat, with the tubular elements of each mat extending across a width of each mat, the second mat having a greater width than the first mat, wherein the first mat and the second mat are rolled together within the housing.

29. The medical device of claim 24 as a heat exchanger, wherein the first fluid is a heat transfer fluid, and wherein the walls of the first tubular elements are impermeable to the heat transfer fluid and to the second fluid.

30. The medical device of claim 24 wherein the first tubular elements are supported solely by the first layer and the second layer of potting material.

* * * * *